US011452757B2

(12) United States Patent
Yoon et al.

(10) Patent No.: US 11,452,757 B2
(45) Date of Patent: Sep. 27, 2022

(54) ANTIBACTERIAL COMPOSITION EFFECTIVE IN TREATING GRAM NEGATIVE BACTERIAL INFECTIONS AND METHOD FOR PREPARING THE SAME

(71) Applicant: iNtRON Biotechnology, Inc., Seongnam-si (KR)

(72) Inventors: Seong Jun Yoon, Seoul (KR); Soo Youn Jun, Seoul (KR); Jeong Won Park, Gyeonggi-do (KR); Ji Hyun Kim, Incheon (KR); Saet Byeol Kim, Gyeonggi-do (KR); Sang Hyeon Kang, Seoul (KR)

(73) Assignee: iNtRON Biotechnology, Inc., Seongnam-si (KR)

( * ) Notice: Subject to any disclaimer, the term of this patent is extended or adjusted under 35 U.S.C. 154(b) by 21 days.

(21) Appl. No.: 17/185,251

(22) Filed: Feb. 25, 2021

(65) Prior Publication Data

US 2022/0265756 A1 Aug. 25, 2022

(51) Int. Cl.

| | |
|---|---|
| ***A61K 38/16*** | (2006.01) |
| ***A61K 38/02*** | (2006.01) |
| ***A61K 47/18*** | (2017.01) |
| ***A61K 47/26*** | (2006.01) |
| ***A61P 31/04*** | (2006.01) |

(52) U.S. Cl.

CPC ............ *A61K 38/02* (2013.01); *A61K 38/162* (2013.01); *A61K 47/183* (2013.01); *A61K 47/26* (2013.01); *A61P 31/04* (2018.01)

(58) Field of Classification Search

None

See application file for complete search history.

(56) References Cited

PUBLICATIONS

NCBI entry YP_006383882, first available 2014.*

* cited by examiner

*Primary Examiner* — Fred H Reynolds

(74) *Attorney, Agent, or Firm* — SIMI Law Group, PC

(57) ABSTRACT

A pharmaceutical composition for treating Gram negative bacteria-associated infections includes an antibacterial protein that includes at least one selected from the group of a protein having the amino acid sequence as set forth in SEQ ID NO: 1, a protein having the amino acid sequence as set forth in SEQ ID NO: 2, a protein having the amino acid sequence as set forth in SEQ ID NO: 3, a protein having the amino acid sequence as set forth in SEQ ID NO: 4, a protein having the amino acid sequence as set forth in SEQ ID NO: 5, a protein having the amino acid sequence as set forth in SEQ ID NO: 6, a protein having the amino acid sequence as set forth in SEQ ID NO: 7, and a protein having the amino acid sequence as set forth in SEQ ID NO: 8. A method of preparing the antibacterial protein is also disclosed.

13 Claims, 2 Drawing Sheets

Specification includes a Sequence Listing.

AP-4

AP-6

ANTIBACTERIAL COMPOSITION EFFECTIVE IN TREATING GRAM NEGATIVE BACTERIAL INFECTIONS AND METHOD FOR PREPARING THE SAME

BACKGROUND OF THE INVENTION

Field of the Invention

The present invention is related to an antibacterial protein having lytic activity to Gram negative bacteria including *Acinetobacter baumannii, Pseudomonas aeruginosa*, and *Klebsiella pneumoniae*. More specifically, the present invention relates to an antibacterial protein that was engineered to effectively work on Gram negative bacteria due to the enhanced outer membrane-penetration efficiency, a pharmaceutical composition effective in treating Gram negative bacteria-associated infections including the same, and a method of preparing the same.

Discussion of the Related Art

Gram negative bacteria are classified by the color they turn after a chemical process called Gram staining is applied. Gram negative bacteria stains turn red when this process is used. Other bacteria stains turn blue, and they are called Gram positive bacteria. Gram negative and Gram positive bacteria stains have different properties because their cell walls are different. They also cause different types of infections, and different types of antibiotics are effective against them. Gram negative infections include those caused by *Acinetobacter baumannii, Pseudomonas aeruginosa, Klebsiella pneumoniae*, as well as many other less common bacteria. Gram negative bacteria cause many serious infections such as pneumonia, peritonitis (inflammation of the membrane that lines the abdominal cavity), urinary tract infections, bloodstream infections, wound or surgical site infections, and meningitis.

In addition to the problem of antibiotic resistance in Gram positive bacteria, such as MRSA (methicillin-resistant *Staphylococcus aureus*) and VRE (vancomycin-resistant Enterococci), the problem of resistance in Gram negative bacteria is also very serious. With the increasing worldwide prevalence of antibiotic-resistant Gram negative bacteria, there is an urgent need for new bactericidal agents effective in treating infections caused by Gram negative bacteria. WHO announced that global measures against *Acinetobacter baumannii* and *Pseudomonas aeruginosa* were essential, especially in the case of Priority Pathogen No. 1, which requires urgent development of novel antibiotics.

Infections caused by Gram negative bacteria are usually treated with antibiotics. Recently, however, Gram negative bacteria have increasingly developed resistance to antibiotics, thereby the therapeutic effects of antibiotics are reduced. To effectively address the infections caused by Gram negative bacteria resistant to existing antibiotics, new antibiotic/antibacterial substances are needed. Notably, it is urgent to develop pharmaceuticals that can provide the rapid therapeutic effects.

SUMMARY OF THE INVENTION

Accordingly, the present invention has been made keeping in mind the problems encountered in the related art and is intended to solve such problems.

In one embodiment, the present invention discloses a pharmaceutical composition for treating Gram negative bacteria-associated infections. The pharmaceutical composition included an antibacterial protein that includes at least one selected from the group of a protein having the amino acid sequence as set forth in SEQ ID NO: 1, a protein having the amino acid sequence as set forth in SEQ ID NO: 2, a protein having the amino acid sequence as set forth in SEQ ID NO: 3, a protein having the amino acid sequence as set forth in SEQ ID NO: 4, a protein having the amino acid sequence as set forth in SEQ ID NO: 5, a protein having the amino acid sequence as set forth in SEQ ID NO: 6, a protein having the amino acid sequence as set forth in SEQ ID NO: 7, and a protein having the amino acid sequence as set forth in SEQ ID NO: 8.

In another embodiment, the antibacterial protein has antibacterial activity against Gram negative bacteria.

In another embodiment, the antibacterial protein has antibacterial activity against *Acinetobacter baumannii, Pseudomonas aeruginosa*, and *Klebsiella pneumoniae*.

In another embodiment, the Gram negative bacteria-associated infections are pneumonia, peritonitis, urinary tract infections, bloodstream infections, wound or surgical site infections, and meningitis.

In another embodiment, the antibacterial protein has a concentration of 0.01-50 mg/mL.

In another embodiment, the pharmaceutical composition further includes L-Histidine, Poloxamer 188 or Polysorbate 20, and Sorbitol or Mannitol.

In another embodiment, L-Histidine has a concentration of 0.1-50 mM, preferably, 1-25 mM, and more preferably, 5-15 mM; Poloxamer 188 has a concentration of 0.01%-10%, preferably 0.05%-5%, and more preferably, 0.25%-0.75%; Polysorbate 20 has a concentration of 0.01%-10%, preferably, 0.02%-2%, and more preferably, 0.05%-0.2%; Sorbitol has a concentration of 0.1%-20%, preferably, 1%-15%, and more preferably, 2.5%-7.5%, and Mannitol has a concentration of 0.1%-20%, preferably, 1%-15%, and more preferably, 2.5%-7.5%.

In another embodiment, L-Histidine has a concentration of 10 mM, Poloxamer 188 has a concentration of 0.5%, Polysorbate 20 has a concentration of 0.1%, Sorbitol has a concentration of 5%, and Mannitol has a concentration of 5%.

In another embodiment, the pharmaceutical composition has a pH value of 5.0 to 7.5.

In another embodiment, the pharmaceutical composition has a pH value of 6.5.

In another embodiment, the pharmaceutical composition is used as antibiotics, disinfectants, germicides, or therapeutic drugs.

In another embodiment, the present application provides a method of preparing an antibacterial protein that includes at least one selected from the group of a protein having the amino acid sequence as set forth in SEQ ID NO: 1, a protein having the amino acid sequence as set forth in SEQ ID NO: 2, a protein having the amino acid sequence as set forth in SEQ ID NO: 3, a protein having the amino acid sequence as set forth in SEQ ID NO: 4, a protein having the amino acid sequence as set forth in SEQ ID NO: 5, a protein having the amino acid sequence as set forth in SEQ ID NO: 6, a protein having the amino acid sequence as set forth in SEQ ID NO: 7, and a protein having the amino acid sequence as set forth in SEQ ID NO: 8. The method includes: culturing *Escherichia coli* cells including a plasmid that comprises a sequence as set forth in SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24; inducing the expression of the antibacterial protein; recovering an inclusion body;

solubilizing the inclusion body; purifying the antibacterial protein; and refolding the antibacterial protein.

In another embodiment, the antibacterial protein has a purity of 90%-99.99%.

It is to be understood that both the foregoing general description and the following detailed description are exemplary and explanatory and are intended to provide further explanation of the invention as claimed.

Advantageous Effects of Invention

In accordance with the present invention, the pharmaceutical composition of the present invention is effective against Gram negative bacteria, especially *Acinetobacter baumannii*, resistant to existing antibiotics or antibacterial substances.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
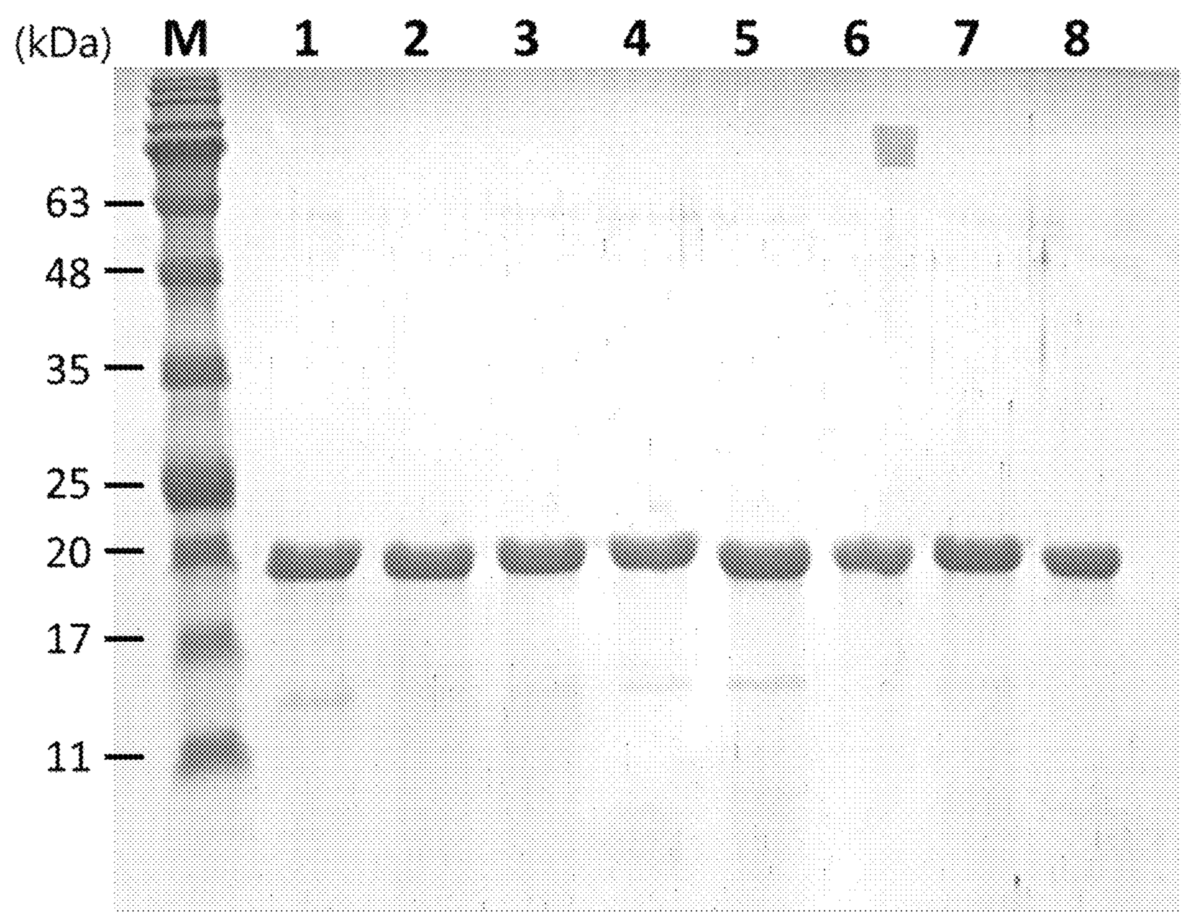
FIG. 1 is an electrophoretic image showing the recombinantly produced antibacterial proteins. Lane M: protein size marker; lane 1: a protein having the amino acid sequence as set forth in SEQ ID NO: 1; lane 2: a protein having the amino acid sequence as set forth in SEQ ID NO: 2; lane 3: a protein with the amino acid sequence as set forth in SEQ ID NO: 3; lane 4: a protein with the amino acid sequence as set forth in SEQ ID NO: 4; lane 5: a protein with the amino acid sequence as set forth in SEQ ID NO: 5; lane 6: a protein with the amino acid sequence as set forth in SEQ ID NO: 6; lane 7: a protein with the amino acid sequence as set forth in SEQ ID NO: 7; and lane 8: a protein with the amino acid sequence as set forth in SEQ ID NO: 8.

Reference will now be made in detail to embodiments of the present invention, example of which is illustrated in the accompanying drawings.

Thus, in accordance with one aspect of the present invention, an antibacterial protein includes at least one selected from the group of a protein having the amino acid sequence as set forth in SEQ ID NO: 1 (AP-1), a protein having the amino acid sequence as set forth in SEQ ID NO: 2 (AP-2), a protein having the amino acid sequence as set forth in SEQ ID NO: 3 (AP-3), a protein having the amino acid sequence as set forth in SEQ ID NO: 4 (AP-4), a protein having the amino acid sequence as set forth in SEQ ID NO: 5 (AP-5), a protein having the amino acid sequence as set forth in SEQ ID NO: 6 (AP-6), a protein having the amino acid sequence as set forth in SEQ ID NO: 7 (AP-7), and a protein having the amino acid sequence as set forth in SEQ ID NO: 8 (AP-8).

The nucleotide sequence encoding the protein AP-1 is set forth in SEQ ID NO: 9; the nucleotide sequence encoding the protein AP-2 is set forth in SEQ ID NO: 10; the nucleotide sequence encoding the protein AP-3 is set forth in SEQ ID NO: 11; the nucleotide sequence encoding the protein AP-4 is set forth in SEQ ID NO: 12; the nucleotide sequence encoding the protein AP-5 is set forth in SEQ ID NO: 13; the nucleotide sequence encoding the protein AP-6 is set forth in SEQ ID NO: 14; the nucleotide sequence encoding the protein AP-7 is set forth in SEQ ID NO: 15; and the nucleotide sequence encoding the protein AP-8 is set forth in SEQ ID NO: 16.

The proteins AP-1, AP-2, AP-3, AP-4, AP-5, AP-6, AP-7, and AP-8 may explicitly and partially be modified by those skilled in the art using the disclosed contents. The said modification includes partial substitution, addition and deletion of one or more amino acids in the amino acid sequences. That being said, it is most desirable to apply correspondingly the amino acid sequences set forth in SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8 as disclosed in the present invention, because the sequences provided in this invention were designed to have the enhanced outer membrane-penetration efficiency based on the applicants' expertise and experience. Specifically, the sequences provided in this invention were designed considering favorable size, hydrophobicity, surface charge, 3-dimensional structure, immunogenicity, etc.

Also, the present invention provides expression plasmids of the proteins AP-1, AP-2, AP-3, AP-4, AP-5, AP-6, AP-7, and AP-8. The expression plasmids including the sequences as set forth in SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24 are available in production of the production hosts of the proteins AP-1, AP-2, AP-3, AP-4, AP-5, AP-6, AP-7, and AP-8.

Also, in accordance with another aspect of the present invention, the present invention provides a pharmaceutical composition. The active ingredient of the pharmaceutical composition is an antibacterial protein includes at least one selected from the group of the proteins AP-1, AP-2, AP-3, AP-4, AP-5, AP-6, AP-7, and AP-8 and can effectively treat infections caused by Gram negative bacteria.

As the active ingredient of the pharmaceutical composition of the present invention, the antibacterial protein is able to specifically lyse Gram negative bacteria, and is effective for treating a range of diseases caused by Gram negative bacteria. Therefore, the pharmaceutical composition of the present invention can treat the diseases caused by Gram negative bacteria. Hence, the pharmaceutical composition of the present invention may be used as antibiotics, disinfectants, germicides and therapeutic drugs, and treat the diseases caused by Gram negative bacteria.

Also, in accordance with another aspect of the present invention, the present invention provides a treatment method for various diseases caused by Gram negative bacteria. The method includes the administration of the composition containing an antibacterial protein includes at least one selected from the group of the proteins AP-1, AP-2, AP-3, AP-4, AP-5, AP-6, AP-7, and AP-8.

Here, the "diseases caused by Gram negative bacteria" collectively refer to the symptoms by infections caused by Gram negative bacteria. The terms "prevention" and "inhibition" used in this specification refer to (i) preventing infections caused by Gram negative bacteria; and (ii) inhibiting the infections caused by Gram negative bacteria from developing into diseases. Also, the term "treating" or "treatment" refers to all actions taken to inhibit the diseases caused by Gram negative bacteria and relieve relevant pathological conditions.

The pharmaceutically acceptable carriers contained in the pharmaceutical composition of the present invention are ordinarily used in preparations, including but not limited to lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methylcellulose, methyl-hydroxybenzoate, propyl hydroxybenzoate, talc, magnesium stearate and mineral oil. In addition to the foregoing ingredients, the pharmaceutical composition of the present invention may include lubricating, wetting, sweetening, flavouring, emulsifying, suspending and preservative agents.

The pharmaceutical composition of the present invention may be administered either orally or non-orally. The non-oral administration may include intravenous, intraperitoneal, intramuscular, subcutaneous or local administration, as well as application or spraying on affected areas.

The pharmaceutical composition of the present invention can be formulated in unit volumes using pharmaceutically acceptable carriers/bulking agents with reference to the method that can be implemented with ease by those skilled in the art of the present invention, or in multi-volume containers. The formulation may take the form of solutions in oil or aqueous media, suspensions or emulsions, or of extracts, powder, granules, tablets or capsules, and may additionally include dispersants or stabilizers.

Also, the appropriate dosage for applying, spraying and administering the foregoing pharmaceutical composition varies with such factors as formulation, administration, age, body weight, severity of symptoms, foods, administration time, administration routes, discharge speed and susceptibility in response. Usually, skilled physicians or veterinarians may decide and prescribe with ease the dosage effective for desired treatments.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Manufacturing of Gram Negative Bacteria-Specific Antibacterial Proteins The proteins AP-1, AP-2, AP-3, AP-4, AP-5, AP-6, AP-7, and AP-8 may be manufactured according to a same manufacturing process.

The proteins AP-1, AP-2, AP-3, AP-4, AP-5, AP-6, AP-7, and AP-8 were prepared as follows. In this example, *Escherichia coli* containing the expression plasmid for Gram negative bacteria-specific antibacterial protein was used as the production strain.

20 μl of *Escherichia coli* production strain was added to 10 ml of the LB medium (Tryptone 10 g/L, Yeast extract 5 g/L, Sodium chloride 10 g/L) with kanamycin (50 μg/ml) prior to an overnight shaking culture at 37° C. The next day, the overnight culture solution was added to the culture medium containing 1 L of the LB medium with kanamycin (50 μg/ml). Then, it was cultured at 37° C. at an agitation of 220 rpm under an aeration condition. Once the cell concentration reached 0.6 in reference to the absorbance at 600 nm, L-arabinose was added until the final concentration reached 0.2% to induce the expression of antibacterial protein, before an additional culture for 4 hours.

Upon completion of the culture, the cell culture solution underwent a centrifugation at 6,000 rpm for 10 minutes at 4° C., and then the cell pellet was harvested. The collected cell pellet was suspended in 20 ml of the PBS (pH 7.2) containing 1 mM EDTA. The cells in the prepared suspension were disrupted with sonication, where 10-second on/10-second off pulses were alternated for 10 minutes to disrupt the cells in an ice bath. After the cell disruption, the lysate solution was centrifuged at 13,000 rpm for 20 minutes at 4° C. to obtain the inclusion body. The obtained inclusion body was resuspended 20 ml of the PBS (pH 7.2) containing 1 mM EDTA then above sonication and centrifugation steps were repeated twice.

The obtained inclusion body was in turn purified through the conventional solubilization and refolding by dialysis, and then subjected to two-step chromatography comprising cation-exchange chromatography and hydrophobic interaction chromatography.

Briefly, the purification process was conducted as follows. In this example, the prepared inclusion body was dissolved in solubilization buffer (6 M Guanidine HCl, 50 mM Tris-HCl, 1 mM EDTA, pH 8.2). After the inclusion body solubilization, the solubilized inclusion body was diluted to 10 fold using a refolding base buffer (880 mM L-arginine, 55 mM Tris-HCl, 22 mM NaCl, 0.88 mM KCl, pH 8.2) and 1% (v/v) refolding additive stocks were added, 100 mM EDTA, 200 mM GSH (reduced glutathione), 100 mM GSSG (oxidized glutathione). After inclusion body refolding, the refolded protein solution was performed to dialysis for salt removal using dialysis buffer (50 mM sodium phosphate, 1 mM EDTA, pH 7.0). Then, the dialyzed supernatant was recovered and subjected to two-step chromatography comprising ion-exchange chromatography using the 5 ml of HiTrap™ SP HP (GE Healthcare, Inc.) and hydrophobic interaction chromatography using 1 ml of HiTrap™ Butyl HP (GE Healthcare, Inc.). In ion-exchange chromatography, the column was pre-equilibrated with the buffer A (50 mM sodium phosphate, 1 mM EDTA, pH 7.0) prior to sample loading. After pre-equilibration, sample loading was performed. Once the sample was loaded onto the column, the buffer C (50 mM sodium phosphate, 1 mM EDTA, 100 mM NaCl, pH 7.0, 10 Column Volume) was flushed at the flow rate of 5 ml/min for washing. After the washing, the chromatography was performed under the condition where the concentration gradient from buffer A to buffer B (50 mM sodium phosphate, 1 mM EDTA, 1 M NaCl, pH 7.0, 20 Column Volume) shifted from 10% to 100%. In the process, the elution fractions containing the antibacterial protein were obtained. In the second hydrophobic interaction chromatography, the column was pre-equilibrated with the buffer A (50 mM sodium phosphate, 1 mM EDTA, 3M NaCl, pH 7.0) prior to loading the elution fraction obtained from ion-exchange chromatography. Once the elution fraction obtained from ion-exchange chromatography was loaded onto the column, the buffer A (10 Column Volume) was flushed at the flow rate of 1 ml/min for washing. After the washing, the chromatography was performed under the condition where the concentration gradient from buffer A to buffer B (50 mM sodium phosphate, 1 mM EDTA, pH 7.0, 30 Column Volume) shifted from 0% to 100%. In the process, the elution fractions containing the antibacterial protein were obtained. Also, more than 90% purity of the antibacterial protein was obtained through the process. FIG. 1 shows the electrophoretic result of the purified antibacterial proteins.

Example 2: Preparation of Pharmaceutical Composition Containing Gram Negative Bacteria-Specific Antibacterial Protein In this example, we prepared the pharmaceutical composition containing the proteins AP-1, AP-2, AP-3, AP-4, AP-5, AP-6, AP-7, and AP-8 manufactured in Example 1 as the active ingredient. The composition presented in this Example is just one of applicable compositions and cannot be said to be exhaustive.

Multiple compositions were prepared using different type of buffers as well as different kinds of stabilizers and additives applicable to pharmaceutical compositions, to explore the composition that could provide an industrially viable stability once the antibacterial protein AP-6 (used as an example) was added. Here, in selecting the buffer, stabilizers and additives, the followings were primarily taken into account: whether these ingredients are pharmaceutically allowed in compliance with the acceptance criteria for medical substances and the isoelectric points of antibacterial protein AP-6.

More specifically, in the stability test, the resistance degree to physical stress including a 2-hour agitation at 2,500 rpm and 16-hour heating at 40° C. was compared with two weeks short-term storage stability. The stability assessment involved the analysis of absorbance measurements and high performance liquid chromatography (HPLC). As a result, the compositions shown in Table 1 below were selected as the formulation appropriate for the antibacterial protein AP-6.

TABLE 1

| | Ingredients |
|---|---|
| Composition 1 | 10 mM L-Histidine, 0.5% (wt) Poloxamer 188, 5% (Wt) Sorbitol, pH 6.5 |
| Composition 2 | 10 mM L-Histidine, 0.5% (wt) Poloxamer 188, 5% (wt) Mannitol, pH 6.5 |
| Composition 3 | 10 mM L-Histidine, 0.1% (wt) Polysorbate 20, 5% (wt) Sorbitol, pH 6.5 |

Next, the appropriateness of the developed formulation to the other antibacterial proteins was examined by analysis of absorbance measurements and high HPLC assay. As result, it was confirmed that the developed three formulations were suitable to the other antibacterial proteins (AP-1, AP-2, AP-3, AP-4, AP-5, AP-7, and AP-8).

To get the final pharmaceutical composition, buffer exchange of antibacterial protein sample obtained in Example 1 was performed with the buffer as per the composition 1 shown in Table 1, and then the final concentration of antibacterial protein was adjusted to 5 mg/ml.

Example 3: Assessing Antibacterial Activity of Gram Negative Bacteria-Specific Antibacterial Proteins Using the pharmaceutical composition (5 mg/ml) prepared in Example 2, we assessed the antibacterial activity of Gram negative bacteria-specific antibacterial proteins against *Acinetobacter baumannii, Pseudomonas aeruginosa*, and *Klebsiella pneumoniae*. The bacterial strain used for this assessment of antibacterial activity were obtained from various institutes, as outlined in Table 2 below.

TABLE 2

| Species | Strain | Source |
|---|---|---|
| *Acinetobacter baumannii* | CCARM 12228 | CCARM |
| *Acinetobacter baumannii* | CCARM 12226 | CCARM |
| *Acinetobacter baumannii* | CCARM 12202 | CCARM |
| *Acinetobacter baumannii* | CCARM 12199 | CCARM |
| *Acinetobacter baumannii* | CCARM 12195 | CCARM |
| *Pseudomonas aeruginosa* | CCARM 2247 | CCARM |
| *Pseudomonas aeruginosa* | CCARM 2252 | CCARM |
| *Pseudomonas aeruginosa* | PA01 (ATCC BAA-47) | ATCC |
| *Pseudomonas aeruginosa* | CCARM 2239 | CCARM |
| *Pseudomonas aeruginosa* | PA1348 | Clinical isolate |
| *Klebsiella pneumoniae* | CCARM 10303 | CCARM |
| *Klebsiella pneumoniae* | CCARM 10263 | CCARM |
| *Klebsiella pneumoniae* | CCARM 10332 | CCARM |
| *Klebsiella pneumoniae* | CCARM 10330 | CCARM |
| *Klebsiella pneumoniae* | KCTC 12385 | KCTC |

CCARM: Culture Collection of Antimicrobial-Resistant Microbes (No. 429 of First Science Hall in Seoul Women's University, 126 Gongneung 2-dong, Nowon-gu, Seoul, Republic of Korea);
ATCC: The American Type Culture Collection (USA);
KCTC: Korea Collection for Type Cultures (181 Ipsin-gil, Jeongeup-si, Jeollabuk-do, Republic of Korea)

Meanwhile, to assess the antibacterial activity to other bacterial species in addition to *Acinetobacter baumannii, Pseudomonas aeruginosa*, and *Klebsiella pneumoniae,* 2 strains of *Streptococcus mutans,* 3 strains of *Enterococcus faecalis*, and 2 strains of *Staphylococcus aureus* were included in the experiment.

The cell lysis assay was used to assess the antibacterial activity. The experimental method of the cell lysis assay is described below. The bacteria were suspended in 20 mM Tris-HCl (pH7.5) to reached around $1\times10^6$ cfu/ml. Then, 0.1 ml of the diluted solution (concentration of antibacterial protein: 25 μg/ml) of the pharmaceutical composition prepared in Example 2 was added to the suspension (0.9 ml). After that, the mixture was incubated for 1 hour at 35° C. After 1-h incubation, cell counting assay was performed.

According to this experimental result, Gram negative bacteria-specific antibacterial proteins exhibited the antibacterial activity only against *Acinetobacter baumannii, Pseudomonas aeruginosa*, and *Klebsiella pneumoniae* bacteria as expected, and had no antibacterial activity to other bacteria tested. This result confirmed that the Gram negative bacteria-specific antibacterial activity of the proteins of the present invention. The experimental results of *Acinetobacter baumannii, Pseudomonas aeruginosa*, and *Klebsiella pneumoniae* bacteria are shown in Table 3.

TABLE 3

| | Relative antibacterial activity | | | | | | | |
|---|---|---|---|---|---|---|---|---|
| Strain | AP-1 | AP-2 | AP-3 | AP-4 | AP-5 | AP-6 | AP-7 | AP-8 |
| *Acinetobacter baumannii* CCARNI 12228 | +++ | +++ | +++ | +++ | +++ | +++ | +++ | +++ |
| *Acinetobacter baumannii* CCARNI 12226 | ++ | +++ | +++ | +++ | +++ | +++ | +++ | +++ |
| *Acinetobacter baumannii* CCARNI 12202 | ++ | +++ | +++ | +++ | +++ | +++ | +++ | +++ |
| *Acinetobacter baumannii* CCARNI 12199 | +++ | +++ | +++ | +++ | +++ | +++ | +++ | +++ |

TABLE 3-continued

| Strain | Relative antibacterial activity | | | | | | | |
|---|---|---|---|---|---|---|---|---|
| | AP-1 | AP-2 | AP-3 | AP-4 | AP-5 | AP-6 | AP-7 | AP-8 |
| *Acinetobacter baumannii* CCARNI 12195 | +++ | +++ | +++ | +++ | +++ | +++ | +++ | +++ |
| *Pseudomonas aeruginosa* CCARNI 2247 | +++ | +++ | +++ | +++ | +++ | +++ | +++ | +++ |
| *Pseudomonas aeruginosa* CCARNI 2252 | +++ | +++ | +++ | +++ | +++ | +++ | +++ | +++ |
| *Pseudomonas aeruginosa* PA01 | +++ | +++ | ++ | ++ | +++ | +++ | +++ | +++ |
| *Pseudomonas aeruginosa* CCARNI 2239 | ++ | +++ | +++ | +++ | +++ | +++ | +++ | +++ |
| *Pseudomonas aeruginosa* PA1348 | +++ | +++ | +++ | +++ | +++ | +++ | +++ | +++ |
| *Klebsiella pneumonia* CCARNI 10303 | − | ++ | ++ | +++ | ++ | +++ | + | +++ |
| *Klebsiella pneumonia* CCARNI 10263 | +++ | +++ | +++ | +++ | +++ | +++ | +++ | +++ |
| *Klebsiella pneumonia* CCARNI 10332 | +++ | +++ | +++ | +++ | +++ | +++ | +++ | +++ |
| *Klebsiella pneumonia* CCARNI 10330 | +++ | +++ | +++ | +++ | +++ | +++ | +++ | +++ |
| *Klebsiella pneumonia* CCARM 12385 | +++ | +++ | ++ | +++ | +++ | +++ | +++ | +++ |

+++: more than "−3 log reduction" in cell count;
++: from more than "−2 log reduction" to less than "−3 log reduction" in cell count;
+: from more than "−1 log reduction" to less than "−2 log reduction" in cell count;
−: less than "−1 log reduction" or "no activity".

These results prove that the Gram negative bacteria-specific antibacterial proteins of the present invention are able to lyse and eventually kill Gram negative bacteria. This antibacterial property suggests the pharmaceutical composition containing Gram negative bacteria-specific antibacterial proteins are applicable to killing Gram negative bacteria in infections caused by Gram negative bacteria, and to treating such infections in the same manner as conventional antibiotics.

Example 4: Assessing Antibacterial Activity of Gram Negative Bacteria-Specific Antibacterial Proteins Against Antibiotic-Resistant Strains Using the pharmaceutical composition (5 mg/ml) prepared in Example 2, we assessed the antibacterial activity of Gram negative bacteria-specific antibacterial proteins against antibiotic-resistant strains.

As Gram negative bacteria-specific antibacterial protein, AP-4 and AP-6 were used, and Meropenem-resistant *Acinetobacter baumannii* strain (CCARM 12208) was used as model strain of antibiotic-resistant Gram negative bacteria.

The antibacterial activity of antibacterial proteins was investigated by typical spot assay (spot-on-lawn assay). Mix 50 μl of bacteria cultured overnight in a TSB culture medium and 4 ml top agar (0.6% agar contained TSB: melt then cool to 50° C.) and dispense onto the TSA plate. After drying, each 20 μl of antibacterial protein solution (0.5 mg/ml) was dropped on each plate. A buffer (PBS) containing no antibacterial protein was dropped as a negative control. After spotting, culture was performed in an incubator at 37° C. for overnight, and the degree of bacteriolysis of bacterium was observed.

Figure 2:
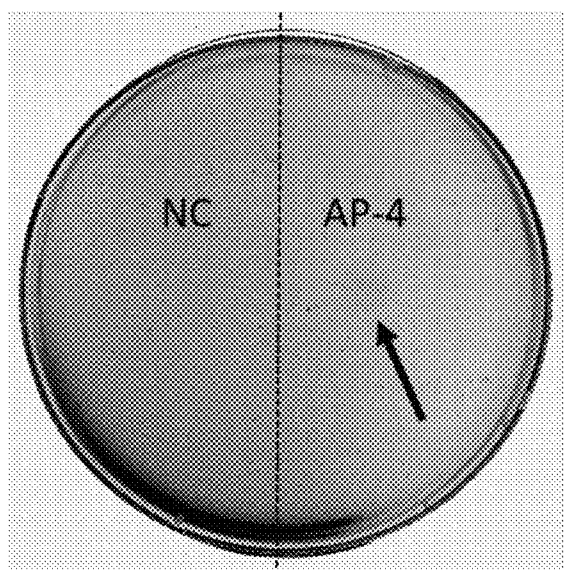
FIG. 2 shows the result of antibacterial activity (bacteriolytic activity) of the antibacterial proteins against antibiotic-resistant bacteria, in which a transparent portion (indicated with arrow) is generated due to the antibacterial activity (bacteriolytic activity) of the antibacterial proteins. NC: negative control.
Figure 2:
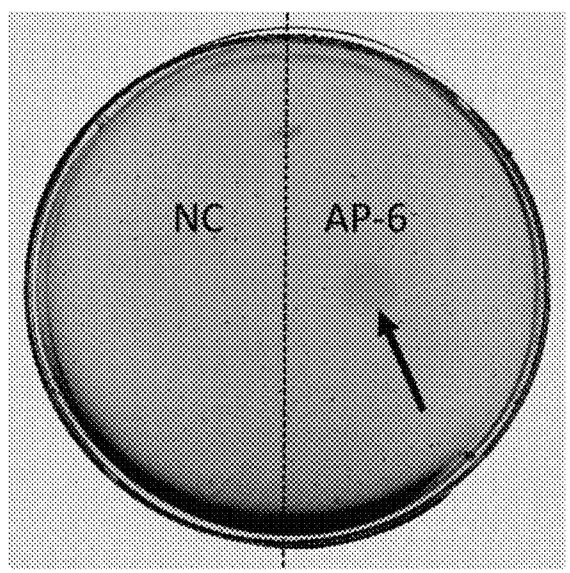

As a result, the antibacterial proteins exhibited strong antibacterial (bacteriolytic) activity for the tested antibiotic-resistant Gram negative bacteria. The experimental results of spot assay are shown in FIG. 2.

From these results, it was confirmed that the antibacterial proteins can provide an excellent bacteriolytic ability against antibiotic-resistant Gram negative bacteria and can be effectively used for the treatment of infectious diseases caused by antibiotic-susceptible and Meropenem-resistant Gram negative bacteria.

Example 5: Assessing Therapeutic Effects of Gram Negative Bacteria-Specific Antibacterial Proteins on Gram Negative Bacteria-Associated Infections Using the pharmaceutical composition (AP-6: 5 mg/ml) prepared in Example 2, we assessed the therapeutic effects of Gram negative bacteria-specific antibacterial protein on the infections caused by Gram negative bacteria using the infected animal model.

In this example, *Acinetobacter baumannii* strain (CCARM 12226) was used as the model pathogen for Gram negative infections. 5-week-old ICR mice [specific pathogen-free (SPF) grade] weighing around 20 g each were used as experimental animals. A total of 20 mice were assigned to two groups (10 mice per each group). Then, $1\times10^8$ cfu of bacteria was administered to each mouse (i.e. $1\times10^8$ cfu/mouse) intravenously to induce infections. One group (treatment group) was given the pharmaceutical composition (AP-6: 5 mg/ml) prepared in Example 2, at the time point of 30 minutes, 12 hours and 24 hours after the bacterial challenging. The dosage was set to 25 mg/kg. To the other group (control group), only the formulation buffer was administered, where the volume of the formulation buffer administered to each animal was equivalent to the mean volume of the pharmaceutical composition administered to the treatment group. As in the administration of the pharmaceutical composition, the formulation buffer was administered at the time point of 30 minutes, 12 hours and 24 hours after the bacterial challenging. For five days following the bacterial challenging, dead individuals were counted each day, and specific responses were checked twice daily in the morning and afternoon.

This experimental result proved the explicit therapeutic effects. As shown in Table 4 below, the dead individual count supports the definite effects on the improved survival rates of the administered pharmaceutical composition containing the Gram negative bacteria-specific antibacterial protein of the present invention. Also, compared with the control group, where diverse specific responses including erythema of lid margin and decreased activity were observed, such specific responses were hardly observed in the treatment group.

TABLE 4

| | Dead individuals Days after bacterial challenging | | | | | Dead individuals/ Tested | Mortality |
|---|---|---|---|---|---|---|---|
| Group | 1 | 2 | 3 | 4 | 5 | individuals | rate (%) |
| Control | 0 | 2 | 2 | 1 | 0 | 5/10 | 50 |
| Treatment | 0 | 0 | 0 | 0 | 0 | 0/10 | 0 |

These results indicate the Gram negative bacteria-specific antibacterial proteins of the present invention are effective for the treatment of infections caused by Gram negative bacteria. Such therapeutic effects suggest the pharmaceutical composition containing Gram negative bacteria-specific antibacterial protein is applicable to treating the infections caused by Gram negative bacteria, and also can be used in the same manner as conventional antibiotics for the treatment of infections caused by Gram negative bacteria.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A pharmaceutical composition for treating Gram negative bacteria-associated infections, comprising an antibacterial protein that includes at least one selected from the group of a protein having the amino acid sequence as set forth in SEQ ID NO: 1, a protein having the amino acid sequence as set forth in SEQ ID NO: 2, a protein having the amino acid sequence as set forth in SEQ ID NO: 3, a protein having the amino acid sequence as set forth in SEQ ID NO: 4, a protein having the amino acid sequence as set forth in SEQ ID NO: 5, a protein having the amino acid sequence as set forth in SEQ ID NO: 6, a protein having the amino acid sequence as set forth in SEQ ID NO: 7, and a protein having the amino acid sequence as set forth in SEQ ID NO: 8.

2. The pharmaceutical composition of claim 1, wherein the antibacterial protein has antibacterial activity against Gram negative bacteria.

3. The pharmaceutical composition of claim 2, wherein the antibacterial protein has antibacterial activity against *Acinetobacter baumannii, Pseudomonas aeruginosa*, and *Klebsiella pneumoniae.*

4. The pharmaceutical composition of claim 1, wherein the Gram negative bacteria-associated infections are pneumonia, peritonitis, urinary tract infections, bloodstream infections, wound or surgical site infections, and meningitis.

5. The pharmaceutical composition of claim 1, wherein the antibacterial protein has a concentration of 0.01-50 mg/mL.

6. The pharmaceutical composition of claim 1, further comprising L-Histidine, Poloxamer 188 or Polysorbate 20, and Sorbitol or Mannitol.

7. The pharmaceutical composition of claim 6, wherein L-Histidine has a concentration of 0.1-50 mM, Poloxamer 188 has a concentration of 0.01%-10%, Polysorbate 20 has a concentration of 0.01%-10%, Sorbitol has a concentration of 0.1%-20%, and Mannitol has a concentration of 0.1%-20%.

8. The pharmaceutical composition of claim 7, wherein L-Histidine has a concentration of 10 mM, Poloxamer 188 has a concentration of 0.5%, Polysorbate 20 has a concentration of 0.1%, Sorbitol has a concentration of 5%, and Mannitol has a concentration of 5%.

9. The pharmaceutical composition of claim 6, wherein the pharmaceutical composition has a pH value of 5.0 to 7.5.

10. The pharmaceutical composition of claim 9, wherein the pharmaceutical composition has a pH value of 6.5.

11. The pharmaceutical composition of claim 1, wherein the pharmaceutical composition is used as antibiotics, disinfectants, germicides, or therapeutic drugs.

12. The pharmaceutical composition of claim 1, wherein the antibacterial protein has a purity of 90%-99.99%.

13. A method of preparing an antibacterial protein that includes at least one selected from the group of a protein having the amino acid sequence as set forth in SEQ ID NO: 1, a protein having the amino acid sequence as set forth in SEQ ID NO: 2, a protein having the amino acid sequence as set forth in SEQ ID NO: 3, a protein having the amino acid sequence as set forth in SEQ ID NO: 4, a protein having the amino acid sequence as set forth in SEQ ID NO: 5, a protein having the amino acid sequence as set forth in SEQ ID NO: 6, a protein having the amino acid sequence as set forth in SEQ ID NO: 7, and a protein having the amino acid sequence as set forth in SEQ ID NO: 8:

culturing *Escherichia coli* cells including a plasmid that comprises a sequence as set forth in SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24;

inducing the expression of the antibacterial protein;

recovering an inclusion body;

solubilizing the inclusion body;

purifying the antibacterial protein; and refolding the antibacterial protein.

* * * * *

SEQUENCE LISTING

```
<160> NUMBER OF SEQ ID NOS: 24

<210> SEQ ID NO 1
<211> LENGTH: 178
<212> TYPE: PRT
<213> ORGANISM: Artificial sequence
<220> FEATURE:
<223> OTHER INFORMATION: Antibacterial protein AP-1

<400> SEQUENCE: 1

Met Ala Met Ser Pro Ala Leu Arg Asn Ser Val Ile Ala Ala Ile Ser
1               5                   10                  15

Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys Tyr Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Asp Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Leu Met Asp Leu
                165                 170                 175

Ala Asp


<210> SEQ ID NO 2
<211> LENGTH: 178
<212> TYPE: PRT
<213> ORGANISM: Artificial sequence
<220> FEATURE:
<223> OTHER INFORMATION: Antibacterial protein AP-2
```

<400> SEQUENCE: 2

```
Met Ala Met Ser Pro Ala Leu Arg Lys Ser Val Ile Ala Ala Ile Ser
1               5                   10                  15

Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys Tyr Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Asp Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Leu Met Asp Leu
                165                 170                 175

Ala Asp
```

<210> SEQ ID NO 3
<211> LENGTH: 178
<212> TYPE: PRT
<213> ORGANISM: Artificial sequence
<220> FEATURE:
<223> OTHER INFORMATION: Antibacterial protein AP-3

<400> SEQUENCE: 3

```
Met Ala Met Ser Pro Ala Leu Arg Asn Ser Val Ile Ala Ala Ile Ser
1               5                   10                  15

Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys His Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Asp Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160
```

```
Val Cys Leu Trp Gly Gln Gln Gly Gly Gly Gly Ser Leu Met Asp Leu
                165                 170                 175

Ala Asp


<210> SEQ ID NO 4
<211> LENGTH: 178
<212> TYPE: PRT
<213> ORGANISM: Artificial sequence
<220> FEATURE:
<223> OTHER INFORMATION: Antibacterial protein AP-4

<400> SEQUENCE: 4

Met Ala Met Ser Pro Ala Leu Arg Asn Ser Val Ile Ala Ala Ile Ser
1               5                   10                  15

Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys Tyr Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Lys Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Leu Met Asp Leu
                165                 170                 175

Ala Asp


<210> SEQ ID NO 5
<211> LENGTH: 178
<212> TYPE: PRT
<213> ORGANISM: Artificial sequence
<220> FEATURE:
<223> OTHER INFORMATION: Antibacterial protein AP-5

<400> SEQUENCE: 5

Met Ala Met Ser Pro Ala Leu Arg Lys Ser Val Ile Ala Ala Ile Ser
1               5                   10                  15

Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys His Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Asp Ile
                85                  90                  95
```

```
Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Leu Met Asp Leu
                165                 170                 175

Ala Asp


<210> SEQ ID NO 6
<211> LENGTH: 178
<212> TYPE: PRT
<213> ORGANISM: Artificial sequence
<220> FEATURE:
<223> OTHER INFORMATION: Antibacterial protein AP-6

<400> SEQUENCE: 6

Met Ala Met Ser Pro Ala Leu Arg Lys Ser Val Ile Ala Ala Ile Ser
1               5                   10                  15

Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys Tyr Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Lys Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Leu Met Asp Leu
                165                 170                 175

Ala Asp


<210> SEQ ID NO 7
<211> LENGTH: 178
<212> TYPE: PRT
<213> ORGANISM: Artificial sequence
<220> FEATURE:
<223> OTHER INFORMATION: Antibacterial protein AP-7

<400> SEQUENCE: 7

Met Ala Met Ser Pro Ala Leu Arg Asn Ser Val Ile Ala Ala Ile Ser
1               5                   10                  15

Gly Gly Ala Ile Ala Ile Ala Ser Val Leu Ile Thr Gly Pro Gly Gly
            20                  25                  30
```

```
Asn Asp Gly Leu Glu Gly Val Arg His Lys Pro Tyr Lys Asp Val Val
        35                  40                  45

Gly Val Leu Thr Val Cys His Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Lys Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Leu Met Asp Leu
                165                 170                 175

Ala Asp


<210> SEQ ID NO 8
<211> LENGTH: 178
<212> TYPE: PRT
<213> ORGANISM: Artificial sequence
<220> FEATURE:
<223> OTHER INFORMATION: Antibacterial protein AP-8

<400> SEQUENCE: 8

Met Ala Met Ser Pro Ala Leu Arg Lys Ser Val Ile Ala Ala Ile Ser
1               5                   10                  15

Gly Gly Ala Ile Ala Ile Ala Ser Val Leu Ile Thr Gly Pro Gly Gly
            20                  25                  30

Asn Asp Gly Leu Glu Gly Val Arg His Lys Pro Tyr Lys Asp Val Val
        35                  40                  45

Gly Val Leu Thr Val Cys His Gly His Val Gly Lys Asp Ile Met Leu
    50                  55                  60

Gly Lys Thr Tyr Thr Glu Ala Glu Cys Lys Ala Leu Leu Asn Lys Asp
65                  70                  75                  80

Leu Ala Thr Val Ala Arg Gln Ile Asn Pro Tyr Ile Lys Val Lys Ile
                85                  90                  95

Pro Glu Thr Thr Arg Gly Ala Leu Tyr Ser Phe Val Tyr Asn Val Gly
            100                 105                 110

Ala Gly Asn Phe Arg Thr Ser Thr Leu Leu Arg Lys Ile Asn Gln Gly
        115                 120                 125

Asp Ile Lys Gly Ala Cys Asp Gln Leu Arg Arg Trp Thr Tyr Ala Gly
    130                 135                 140

Gly Lys Gln Trp Lys Gly Leu Met Thr Arg Arg Glu Ile Glu Arg Glu
145                 150                 155                 160

Val Cys Leu Trp Gly Gln Gln Gly Gly Gly Gly Ser Leu Met Asp Leu
                165                 170                 175

Ala Asp


<210> SEQ ID NO 9
<211> LENGTH: 537
<212> TYPE: DNA
<213> ORGANISM: Artificial sequence
```

<220> FEATURE:
<223> OTHER INFORMATION: Antibacterial protein AP-1

<400> SEQUENCE: 9
atggcaatgt caccggcact acgaaatagc gtaatagcgg cgataagtgg cggggctatt 60
gccatagcat ctgtgttaat cactggcccc ggtggtaacg atggtctgga aggtgtcaga 120
cacaaaccat acaaggacgt agttggtgtg ttgactgtgt gttatggcca cgtcggaaaa 180
gacatcatgc tcggtaaaac gtataccgaa gcagaatgca aagccctcct gaataaagac 240
cttgccacgg tcgccagaca aattaacccg tacatcaaag tcgatatacc ggaaacaacg 300
cgcggcgctc tttattcgtt cgtctataac gtgggcgcag gcaatttcag aacatcgacg 360
cttcttcgca aaatcaacca gggcgatatc aagggcgcat gtgaccagct acgtcgctgg 420
acatacgctg gcggtaagca atggaaaggg ctgatgactc gccgtgagat tgagcgtgaa 480
gtctgtttgt gggggcagca aggcggaggg ggctcgctga tggatctggc ggattaa 537

<210> SEQ ID NO 10
<211> LENGTH: 537
<212> TYPE: DNA
<213> ORGANISM: Artificial sequence
<220> FEATURE:
<223> OTHER INFORMATION: Antibacterial protein AP-2

<400> SEQUENCE: 10
atggcaatgt caccggcact acgaaaaagc gtaatagcgg cgataagtgg cggggctatt 60
gccatagcat ctgtgttaat cactggcccc ggtggtaacg atggtctgga aggtgtcaga 120
cacaaaccat acaaggacgt agttggtgtg ttgactgtgt gttatggcca cgtcggaaaa 180
gacatcatgc tcggtaaaac gtataccgaa gcagaatgca aagccctcct gaataaagac 240
cttgccacgg tcgccagaca aattaacccg tacatcaaag tcgatatacc ggaaacaacg 300
cgcggcgctc tttattcgtt cgtctataac gtgggcgcag gcaatttcag aacatcgacg 360
cttcttcgca aaatcaacca gggcgatatc aagggcgcat gtgaccagct acgtcgctgg 420
acatacgctg gcggtaagca atggaaaggg ctgatgactc gccgtgagat tgagcgtgaa 480
gtctgtttgt gggggcagca aggcggaggg ggctcgctga tggatctggc ggattaa 537

<210> SEQ ID NO 11
<211> LENGTH: 537
<212> TYPE: DNA
<213> ORGANISM: Artificial sequence
<220> FEATURE:
<223> OTHER INFORMATION: Antibacterial protein AP-3

<400> SEQUENCE: 11
atggcaatgt caccggcact acgaaatagc gtaatagcgg cgataagtgg cggggctatt 60
gccatagcat ctgtgttaat cactggcccc ggtggtaacg atggtctgga aggtgtcaga 120
cacaaaccat acaaggacgt agttggtgtg ttgactgtgt gtcatggcca cgtcggaaaa 180
gacatcatgc tcggtaaaac gtataccgaa gcagaatgca aagccctcct gaataaagac 240
cttgccacgg tcgccagaca aattaacccg tacatcaaag tcgatatacc ggaaacaacg 300
cgcggcgctc tttattcgtt cgtctataac gtgggcgcag gcaatttcag aacatcgacg 360
cttcttcgca aaatcaacca gggcgatatc aagggcgcat gtgaccagct acgtcgctgg 420
acatacgctg gcggtaagca atggaaaggg ctgatgactc gccgtgagat tgagcgtgaa 480
gtctgtttgt gggggcagca aggcggaggg ggctcgctga tggatctggc ggattaa 537

<210> SEQ ID NO 12
<211> LENGTH: 537
<212> TYPE: DNA
<213> ORGANISM: Artificial sequence
<220> FEATURE:
<223> OTHER INFORMATION: Antibacterial protein AP-4

<400> SEQUENCE: 12
atggcaatgt caccggcact acgaaatagc gtaatagcgg cgataagtgg cggggctatt 60
gccatagcat ctgtgttaat cactggcccc ggtggtaacg atggtctgga aggtgtcaga 120
cacaaaccat acaaggacgt agttggtgtg ttgactgtgt gttatggcca cgtcggaaaa 180
gacatcatgc tcggtaaaac gtataccgaa gcagaatgca aagccctcct gaataaagac 240
cttgccacgg tcgccagaca aattaacccg tacatcaaag tcaaaatacc ggaaacaacg 300
cgcggcgctc tttattcgtt cgtctataac gtgggcgcag gcaatttcag aacatcgacg 360
cttcttcgca aaatcaacca gggcgatatc aagggcgcat gtgaccagct acgtcgctgg 420
acatacgctg gcggtaagca atggaaaggg ctgatgactc gccgtgagat tgagcgtgaa 480
gtctgtttgt gggggcagca aggcggaggg ggctcgctga tggatctggc ggattaa 537

<210> SEQ ID NO 13
<211> LENGTH: 537
<212> TYPE: DNA
<213> ORGANISM: Artificial sequence
<220> FEATURE:
<223> OTHER INFORMATION: Antibacterial protein AP-5

<400> SEQUENCE: 13
atggcaatgt caccggcact acgaaaaagc gtaatagcgg cgataagtgg cggggctatt 60
gccatagcat ctgtgttaat cactggcccc ggtggtaacg atggtctgga aggtgtcaga 120
cacaaaccat acaaggacgt agttggtgtg ttgactgtgt gtcatggcca cgtcggaaaa 180
gacatcatgc tcggtaaaac gtataccgaa gcagaatgca aagccctcct gaataaagac 240
cttgccacgg tcgccagaca aattaacccg tacatcaaag tcgatatacc ggaaacaacg 300
cgcggcgctc tttattcgtt cgtctataac gtgggcgcag gcaatttcag aacatcgacg 360
cttcttcgca aaatcaacca gggcgatatc aagggcgcat gtgaccagct acgtcgctgg 420
acatacgctg gcggtaagca atggaaaggg ctgatgactc gccgtgagat tgagcgtgaa 480
gtctgtttgt gggggcagca aggcggaggg ggctcgctga tggatctggc ggattaa 537

<210> SEQ ID NO 14
<211> LENGTH: 537
<212> TYPE: DNA
<213> ORGANISM: Artificial sequence
<220> FEATURE:
<223> OTHER INFORMATION: Antibacterial protein AP-6

<400> SEQUENCE: 14
atggcaatgt caccggcact acgaaaaagc gtaatagcgg cgataagtgg cggggctatt 60
gccatagcat ctgtgttaat cactggcccc ggtggtaacg atggtctgga aggtgtcaga 120
cacaaaccat acaaggacgt agttggtgtg ttgactgtgt gttatggcca cgtcggaaaa 180
gacatcatgc tcggtaaaac gtataccgaa gcagaatgca aagccctcct gaataaagac 240
cttgccacgg tcgccagaca aattaacccg tacatcaaag tcaaaatacc ggaaacaacg 300
cgcggcgctc tttattcgtt cgtctataac gtgggcgcag gcaatttcag aacatcgacg 360
cttcttcgca aaatcaacca gggcgatatc aagggcgcat gtgaccagct acgtcgctgg 420

```
acatacgctg gcggtaagca atggaaaggg ctgatgactc gccgtgagat tgagcgtgaa    480

gtctgtttgt gggggcagca aggcggaggg ggctcgctga tggatctggc ggattaa       537


<210> SEQ ID NO 15
<211> LENGTH: 537
<212> TYPE: DNA
<213> ORGANISM: Artificial sequence
<220> FEATURE:
<223> OTHER INFORMATION: Antibacterial protein AP-7

<400> SEQUENCE: 15

atggcaatgt caccggcact acgaaatagc gtaatagcgg cgataagtgg cggggctatt     60

gccatagcat ctgtgttaat cactggcccc ggtggtaacg atggtctgga aggtgtcaga    120

cacaaaccat acaaggacgt agttggtgtg ttgactgtgt gtcatggcca cgtcggaaaa    180

gacatcatgc tcggtaaaac gtataccgaa gcagaatgca aagccctcct gaataaagac    240

cttgccacgg tcgccagaca aattaacccg tacatcaaag tcaaaatacc ggaaacaacg    300

cgcggcgctc tttattcgtt cgtctataac gtgggcgcag gcaatttcag aacatcgacg    360

cttcttcgca aaatcaacca gggcgatatc aagggcgcat gtgaccagct acgtcgctgg    420

acatacgctg gcggtaagca atggaaaggg ctgatgactc gccgtgagat tgagcgtgaa    480

gtctgtttgt gggggcagca aggcggaggg ggctcgctga tggatctggc ggattaa       537


<210> SEQ ID NO 16
<211> LENGTH: 537
<212> TYPE: DNA
<213> ORGANISM: Artificial sequence
<220> FEATURE:
<223> OTHER INFORMATION: Antibacterial protein AP-8

<400> SEQUENCE: 16

atggcaatgt caccggcact acgaaaaagc gtaatagcgg cgataagtgg cggggctatt     60

gccatagcat ctgtgttaat cactggcccc ggtggtaacg atggtctgga aggtgtcaga    120

cacaaaccat acaaggacgt agttggtgtg ttgactgtgt gtcatggcca cgtcggaaaa    180

gacatcatgc tcggtaaaac gtataccgaa gcagaatgca aagccctcct gaataaagac    240

cttgccacgg tcgccagaca aattaacccg tacatcaaag tcaaaatacc ggaaacaacg    300

cgcggcgctc tttattcgtt cgtctataac gtgggcgcag gcaatttcag aacatcgacg    360

cttcttcgca aaatcaacca gggcgatatc aagggcgcat gtgaccagct acgtcgctgg    420

acatacgctg gcggtaagca atggaaaggg ctgatgactc gccgtgagat tgagcgtgaa    480

gtctgtttgt gggggcagca aggcggaggg ggctcgctga tggatctggc ggattaa       537


<210> SEQ ID NO 17
<211> LENGTH: 4602
<212> TYPE: DNA
<213> ORGANISM: Artificial sequence
<220> FEATURE:
<223> OTHER INFORMATION: Expression plasmid for antibacterial protein
      AP-1

<400> SEQUENCE: 17

aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240
```

-continued

```
atcctacctg acgcttttta tcgcaactct ctactgtttc tccatacccg tttttttggg    300
ctagaaataa ttttgtttaa ctttaagaag gagatataca tatggcaatg tcaccggcac    360
tacgaaatag cgtaatagcg gcgataagtg gcggggctat tgccatagca tctgtgttaa    420
tcactggccc cggtggtaac gatggtctgg aaggtgtcag acacaaacca tacaaggacg    480
tagttggtgt gttgactgtg tgttatggcc acgtcggaaa agacatcatg ctcggtaaaa    540
cgtataccga agcagaatgc aaagccctcc tgaataaaga ccttgccacg gtcgccagac    600
aaattaaccc gtacatcaaa gtcgatatac cggaaacaac gcgcggcgct ctttattcgt    660
tcgtctataa cgtgggcgca ggcaatttca gaacatcgac gcttcttcgc aaaatcaacc    720
agggcgatat caagggcgca tgtgaccagc tacgtcgctg gacatacgct ggcggtaagc    780
aatggaaagg gctgatgact cgccgtgaga ttgagcgtga agtctgtttg tgggggcagc    840
aaggcggagg gggctcgctg atggatctgg cggattaagc ggccgcaagg gcgagcttga    900
aggtaagcct atccctaacc ctctcctcgg tctcgattct acgcgtaccg gtcatcatca    960
ccatcaccat tgagtttaaa cggtctccag cttggctgtt ttggcggatg agagaagatt   1020
ttcagcctga tacagattaa atcagaacgc agaagcggtc tgataaaaca gaatttgcct   1080
ggcggcagta gcgcggtggt cccacctgac cccatgccga actcagaagt gaaacgccgt   1140
agcgccgatg gtagtgtggg gtctccccat gcgagagtag ggaactgcca ggcatcaaat   1200
aaaacgaaag gctcagtcga aagactgggc ctttcgtttt atctgttgtt tgtcggtgaa   1260
cgctctcctg agtaggacaa atccgccggg agcggatttg aacgttgcga agcaacggcc   1320
cggagggtgg cgggcaggac gcccgccata aactgccagg catcaaatta agcagaaggc   1380
catcctgacg gatggccttt ttgcgtttct acaaactctt ttgtttattt ttctaaatac   1440
attcaaatat gtatccgctc atgagattat caaaaaggat cttcacctag atccttttaa   1500
attaaaaatg aagttttaaa tcaatctaaa gtatatatga gtaaacttgg tctgacagtt   1560
aggcgtcgct tggtcggtca tttcgaaccc cagagtcccg ctcagaagaa ctcgtcaaga   1620
aggcgataga aggcgatgcg ctgcgaatcg ggagcggcga taccgtaaag cacgaggaag   1680
cggtcagccc attcgccgcc aagctcttca gcaatatcac gggtagccaa cgctatgtcc   1740
tgatagcggt ccgccacacc cagccggcca cagtcgatga atccagaaaa gcggccattt   1800
tccaccatga tattcggcaa gcaggcatcg ccatgtgtca cgacgagatc ctcgccgtcg   1860
ggcatgcgcg ccttgagcct ggcgaacagt tcggctggcg cgagcccctg atgctcttcg   1920
tccagatcat cctgatcgac aagaccggct tccatccgag tacgtgctcg ctcgatgcga   1980
tgtttcgctt ggtggtcgaa tgggcaggta gccggatcaa gcgtatgcag ccgccgcatt   2040
gcatcagcca tgatggatac tttctcggca ggagcaaggt gagatgacag gagatcctgc   2100
cccggcactt cgcccaatag cagccagtcc cttcccgctt cagtgacaac gtcgagcaca   2160
gctgcgcaag gaacgcccgt cgtggccagc cacgatagcc gcgctgcctc gtcctgcagt   2220
tcattcaggg caccggacag gtcggtcttg acaaaaagaa ccgggcgccc ctgcgctgac   2280
agccggaaca cggcggcatc agagcagccg attgtcagtt gtgcccagtc atagccgaat   2340
agcctctcca cccaagcggc cggagaacct gcgtgcaatc catcttgttc aatcatactc   2400
ttcctttttc aatattattg aagcatttat cagggttatt gtctcatgac caaaatccct   2460
taacgtgagt tttcgttcca ctgagcgtca gaccccgtag aaaagatcaa aggatcttct   2520
tgagatcctt tttttctgcg cgtaatctgc tgcttgcaaa caaaaaaacc accgctacca   2580
gcggtggttt gtttgccgga tcaagagcta ccaactcttt ttccgaaggt aactggcttc   2640
```

```
agcagagcgc agataccaaa tactgtcctt ctagtgtagc cgtagttagg ccaccacttc   2700

aagaactctg tagcaccgcc tacatacctc gctctgctaa tcctgttacc agtggctgct   2760

gccagtggcg ataagtcgtg tcttaccggg ttggactcaa gacgatagtt accggataag   2820

gcgcagcggt cgggctgaac ggggggttcg tgcacacagc ccagcttgga gcgaacgacc   2880

tacaccgaac tgagatacct acagcgtgag ctatgagaaa gcgccacgct tcccgaaggg   2940

agaaaggcgg acaggtatcc ggtaagcggc agggtcggaa caggagagcg cacgagggag   3000

cttccagggg gaaacgcctg gtatctttat agtcctgtcg ggtttcgcca cctctgactt   3060

gagcgtcgat ttttgtgatg ctcgtcaggg gggcggagcc tatggaaaaa cgccagcaac   3120

gcggcctttt tacggttcct ggccttttgc tggccttttg ctcacatgtt ctttcctgcg   3180

ttatcccctg attctgtgga taaccgtatt accgcctttg agtgagctga taccgctcgc   3240

cgcagccgaa cgaccgagcg cagcgagtca gtgagcgagg aagcggaaga gcgcctgatg   3300

cggtattttc tccttacgca tctgtgcggt atttcacacc gcatatggtg cactctcagt   3360

acaatctgct ctgatgccgc atagttaagc cagtatacac tccgctatcg ctacgtgact   3420

gggtcatggc tgcgccccga cacccgccaa cacccgctga cgcgccctga cgggcttgtc   3480

tgctcccggc atccgcttac agacaagctg tgaccgtctc cgggagctgc atgtgtcaga   3540

ggttttcacc gtcatcaccg aaacgcgcga ggcagcagat caattcgcgc gcgaaggcga   3600

agcggcatgc ataatgtgcc tgtcaaatgg acgaagcagg gattctgcaa accctatgct   3660

actccgtcaa gccgtcaatt gtctgattcg ttaccaatta tgacaacttg acggctacat   3720

cattcacttt ttcttcacaa ccggcacgga actcgctcgg gctggccccg gtgcattttt   3780

taaatacccg cgagaaatag agttgatcgt caaaaccaac attgcgaccg acggtggcga   3840

taggcatccg ggtggtgctc aaaagcagct tcgcctggct gatacgttgg tcctcgcgcc   3900

agcttaagac gctaatccct aactgctggc ggaaaagatg tgacagacgc gacggcgaca   3960

agcaaacatg ctgtgcgacg ctggcgatat caaaattgct gtctgccagg tgatcgctga   4020

tgtactgaca agcctcgcgt acccgattat ccatcggtgg atggagcgac tcgttaatcg   4080

cttccatgcg ccgcagtaac aattgctcaa gcagatttat cgccagcagc tccgaatagc   4140

gcccttcccc ttgcccggcg ttaatgattt gcccaaacag gtcgctgaaa tgcggctggt   4200

gcgcttcatc cgggcgaaag aaccccgtat tggcaaatat tgacggccag ttaagccatt   4260

catgccagta ggcgcgcgga cgaaagtaaa cccactggtg ataccattcg cgagcctccg   4320

gatgacgacc gtagtgatga atctctcctg gcgggaacag caaaatatca cccggtcggc   4380

aaacaaattc tcgtccctga tttttcacca ccccctgacc gcgaatggtg agattgagaa   4440

tataaccttt cattcccagc ggtcggtcga taaaaaaatc gagataaccg ttggcctcaa   4500

tcggcgttaa acccgccacc agatgggcat taaacgagta tcccggcagc aggggatcat   4560

tttgcgcttc agccatactt ttcatactcc cgccattcag ag                      4602
```

<210> SEQ ID NO 18
<211> LENGTH: 4602
<212> TYPE: DNA
<213> ORGANISM: Artificial sequence
<220> FEATURE:
<223> OTHER INFORMATION: Expression plasmid for antibacterial protein
AP-2

<400> SEQUENCE: 18

```
aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcctacctg acgcttttta tcgcaactct ctactgtttc tccatacccg tttttttggg    300
ctagaaataa ttttgtttaa ctttaagaag gagatataca tatggcaatg tcaccggcac    360
tacgaaaaag cgtaatagcg gcgataagtg gcggggctat tgccatagca tctgtgttaa    420
tcactggccc cggtggtaac gatggtctgg aaggtgtcag acacaaacca tacaaggacg    480
tagttggtgt gttgactgtg tgttatggcc acgtcggaaa agacatcatg ctcggtaaaa    540
cgtataccga agcagaatgc aaagccctcc tgaataaaga ccttgccacg gtcgccagac    600
aaattaaccc gtacatcaaa gtcgatatac cggaaacaac gcgcggcgct ctttattcgt    660
tcgtctataa cgtgggcgca ggcaatttca gaacatcgac gcttcttcgc aaaatcaacc    720
agggcgatat caagggcgca tgtgaccagc tacgtcgctg gacatacgct ggcggtaagc    780
aatggaaagg gctgatgact cgccgtgaga ttgagcgtga agtctgtttg tgggggcagc    840
aaggcggagg gggctcgctg atggatctgg cggattaagc ggccgcaagg gcgagcttga    900
aggtaagcct atccctaacc ctctcctcgg tctcgattct acgcgtaccg gtcatcatca    960
ccatcaccat tgagtttaaa cggtctccag cttggctgtt ttggcggatg agagaagatt   1020
ttcagcctga tacagattaa atcagaacgc agaagcggtc tgataaaaca gaatttgcct   1080
ggcggcagta gcgcggtggt cccacctgac cccatgccga actcagaagt gaaacgccgt   1140
agcgccgatg gtagtgtggg gtctccccat gcgagagtag ggaactgcca ggcatcaaat   1200
aaaacgaaag gctcagtcga aagactgggc ctttcgtttt atctgttgtt tgtcggtgaa   1260
cgctctcctg agtaggacaa atccgccggg agcggatttg aacgttgcga agcaacggcc   1320
cggagggtgg cgggcaggac gcccgccata aactgccagg catcaaatta agcagaaggc   1380
catcctgacg gatggccttt ttgcgtttct acaaactctt ttgtttattt ttctaaatac   1440
attcaaatat gtatccgctc atgagattat caaaaaggat cttcacctag atccttttaa   1500
attaaaaatg aagttttaaa tcaatctaaa gtatatatga gtaaacttgg tctgacagtt   1560
aggcgtcgct tggtcggtca tttcgaaccc cagagtcccg ctcagaagaa ctcgtcaaga   1620
aggcgataga aggcgatgcg ctgcgaatcg ggagcggcga taccgtaaag cacgaggaag   1680
cggtcagccc attcgccgcc aagctcttca gcaatatcac gggtagccaa cgctatgtcc   1740
tgatagcggt ccgccacacc cagccggcca cagtcgatga atccagaaaa gcggccattt   1800
tccaccatga tattcggcaa gcaggcatcg ccatgtgtca cgacgagatc ctcgccgtcg   1860
ggcatgcgcg ccttgagcct ggcgaacagt tcggctggcg cgagcccctg atgctcttcg   1920
tccagatcat cctgatcgac aagaccggct tccatccgag tacgtgctcg ctcgatgcga   1980
tgtttcgctt ggtggtcgaa tgggcaggta gccggatcaa gcgtatgcag ccgccgcatt   2040
gcatcagcca tgatggatac tttctcggca ggagcaaggt gagatgacag gagatcctgc   2100
cccggcactt cgcccaatag cagccagtcc cttcccgctt cagtgacaac gtcgagcaca   2160
gctgcgcaag gaacgcccgt cgtggccagc cacgatagcc gcgctgcctc gtcctgcagt   2220
tcattcaggg caccggacag gtcggtcttg acaaaaagaa ccgggcgccc ctgcgctgac   2280
agccggaaca cggcggcatc agagcagccg attgtcagtt gtgcccagtc atagccgaat   2340
```

-continued

```
agcctctcca cccaagcggc cggagaacct gcgtgcaatc catcttgttc aatcatactc   2400
ttcctttttc aatattattg aagcatttat cagggttatt gtctcatgac caaaatccct   2460
taacgtgagt tttcgttcca ctgagcgtca gaccccgtag aaaagatcaa aggatcttct   2520
tgagatcctt tttttctgcg cgtaatctgc tgcttgcaaa caaaaaaacc accgctacca   2580
gcggtggttt gtttgccgga tcaagagcta ccaactcttt ttccgaaggt aactggcttc   2640
agcagagcgc agataccaaa tactgtcctt ctagtgtagc cgtagttagg ccaccacttc   2700
aagaactctg tagcaccgcc tacatacctc gctctgctaa tcctgttacc agtggctgct   2760
gccagtggcg ataagtcgtg tcttaccggg ttggactcaa gacgatagtt accggataag   2820
gcgcagcggt cgggctgaac ggggggttcg tgcacacagc ccagcttgga gcgaacgacc   2880
tacaccgaac tgagatacct acagcgtgag ctatgagaaa gcgccacgct tcccgaaggg   2940
agaaaggcgg acaggtatcc ggtaagcggc agggtcggaa caggagagcg cacgagggag   3000
cttccagggg gaaacgcctg gtatctttat agtcctgtcg ggtttcgcca cctctgactt   3060
gagcgtcgat ttttgtgatg ctcgtcaggg gggcggagcc tatggaaaaa cgccagcaac   3120
gcggcctttt tacggttcct ggccttttgc tggccttttg ctcacatgtt ctttcctgcg   3180
ttatcccctg attctgtgga taaccgtatt accgcctttg agtgagctga taccgctcgc   3240
cgcagccgaa cgaccgagcg cagcgagtca gtgagcgagg aagcggaaga gcgcctgatg   3300
cggtattttc tccttacgca tctgtgcggt atttcacacc gcatatggtg cactctcagt   3360
acaatctgct ctgatgccgc atagttaagc cagtatacac tccgctatcg ctacgtgact   3420
gggtcatggc tgcgccccga cacccgccaa cacccgctga cgcgccctga cgggcttgtc   3480
tgctcccggc atccgcttac agacaagctg tgaccgtctc cgggagctgc atgtgtcaga   3540
ggttttcacc gtcatcaccg aaacgcgcga ggcagcagat caattcgcgc gcgaaggcga   3600
agcggcatgc ataatgtgcc tgtcaaatgg acgaagcagg gattctgcaa accctatgct   3660
actccgtcaa gccgtcaatt gtctgattcg ttaccaatta tgacaacttg acggctacat   3720
cattcacttt ttcttcacaa ccggcacgga actcgctcgg gctggccccg gtgcattttt   3780
taaatacccg cgagaaatag agttgatcgt caaaaccaac attgcgaccg acggtggcga   3840
taggcatccg ggtggtgctc aaaagcagct tcgcctggct gatacgttgg tcctcgcgcc   3900
agcttaagac gctaatccct aactgctggc ggaaaagatg tgacagacgc gacggcgaca   3960
agcaaacatg ctgtgcgacg ctggcgatat caaaattgct gtctgccagg tgatcgctga   4020
tgtactgaca agcctcgcgt acccgattat ccatcggtgg atggagcgac tcgttaatcg   4080
cttccatgcg ccgcagtaac aattgctcaa gcagatttat cgccagcagc tccgaatagc   4140
gcccttcccc ttgcccggcg ttaatgattt gcccaaacag gtcgctgaaa tgcggctggt   4200
gcgcttcatc cgggcgaaag aaccccgtat tggcaaatat tgacggccag ttaagccatt   4260
catgccagta ggcgcgcgga cgaaagtaaa cccactggtg ataccattcg cgagcctccg   4320
gatgacgacc gtagtgatga atctctcctg gcgggaacag caaaatatca cccggtcggc   4380
aaacaaattc tcgtccctga tttttcacca ccccctgacc gcgaatggtg agattgagaa   4440
tataaccttt cattcccagc ggtcggtcga taaaaaaatc gagataaccg ttggcctcaa   4500
tcggcgttaa acccgccacc agatgggcat taaacgagta tcccggcagc aggggatcat   4560
tttgcgcttc agccatactt ttcatactcc cgccattcag ag                      4602
```

<210> SEQ ID NO 19
<211> LENGTH: 4602
<212> TYPE: DNA
<213> ORGANISM: Artificial sequence
<220> FEATURE:
<223> OTHER INFORMATION: Expression plasmid for antibacterial protein AP-3

<400> SEQUENCE: 19

```
aagaaaccaa ttgtccatat tgcatcagac attgccgtca ctgcgtcttt tactggctct     60
tctcgctaac caaaccggta accccgctta ttaaaagcat tctgtaacaa agcgggacca    120
aagccatgac aaaaacgcgt aacaaaagtg tctataatca cggcagaaaa gtccacattg    180
attatttgca cggcgtcaca ctttgctatg ccatagcatt tttatccata agattagcgg    240
atcctacctg acgcttttta tcgcaactct ctactgtttc tccatacccg tttttttggg    300
ctagaaataa ttttgtttaa ctttaagaag gagatataca tatggcaatg tcaccggcac    360
tacgaaatag cgtaatagcg gcgataagtg gcggggctat tgccatagca tctgtgttaa    420
tcactggccc cggtggtaac gatggtctgg aaggtgtcag acacaaacca tacaaggacg    480
tagttggtgt gttgactgtg tgtcatggcc acgtcggaaa agacatcatg ctcggtaaaa    540
cgtataccga agcagaatgc aaagccctcc tgaataaaga ccttgccacg gtcgccagac    600
aaattaaccc gtacatcaaa gtcgatatac cggaaacaac gcgcggcgct ctttattcgt    660
tcgtctataa cgtgggcgca ggcaatttca gaacatcgac gcttcttcgc aaaatcaacc    720
agggcgatat caagggcgca tgtgaccagc tacgtcgctg gacatacgct ggcggtaagc    780
aatggaaagg gctgatgact cgccgtgaga ttgagcgtga agtctgtttg tgggggcagc    840
aaggcggagg gggctcgctg atggatctgg cggattaagc ggccgcaagg gcgagcttga    900
aggtaagcct atccctaacc ctctcctcgg tctcgattct acgcgtaccg gtcatcatca    960
ccatcaccat tgagtttaaa cggtctccag cttggctgtt ttggcggatg agagaagatt   1020
ttcagcctga tacagattaa atcagaacgc agaagcggtc tgataaaaca gaatttgcct   1080
ggcggcagta gcgcggtggt cccacctgac cccatgccga actcagaagt gaaacgccgt   1140
agcgccgatg gtagtgtggg gtctccccat gcgagagtag ggaactgcca ggcatcaaat   1200
aaaacgaaag gctcagtcga aagactgggc ctttcgtttt atctgttgtt tgtcggtgaa   1260
cgctctcctg agtaggacaa atccgccggg agcggatttg aacgttgcga agcaacggcc   1320
cggagggtgg cgggcaggac gcccgccata aactgccagg catcaaatta agcagaaggc   1380
catcctgacg gatggccttt ttgcgtttct acaaactctt ttgtttattt ttctaaatac   1440
attcaaatat gtatccgctc atgagattat caaaaaggat cttcacctag atccttttaa   1500
attaaaaatg aagttttaaa tcaatctaaa gtatatatga gtaaacttgg tctgacagtt   1560
aggcgtcgct tggtcggtca tttcgaaccc cagagtcccg ctcagaagaa ctcgtcaaga   1620
aggcgataga aggcgatgcg ctgcgaatcg ggagcggcga taccgtaaag cacgaggaag   1680
cggtcagccc attcgccgcc aagctcttca gcaatatcac gggtagccaa cgctatgtcc   1740
tgatagcggt ccgccacacc cagccggcca cagtcgatga atccagaaaa gcggccattt   1800
tccaccatga tattcggcaa gcaggcatcg ccatgtgtca cgacgagatc ctcgccgtcg   1860
ggcatgcgcg ccttgagcct ggcgaacagt tcggctggcg cgagcccctg atgctcttcg   1920
tccagatcat cctgatcgac aagaccggct tccatccgag tacgtgctcg ctcgatgcga   1980
tgtttcgctt ggtggtcgaa tgggcaggta gccggatcaa gcgtatgcag ccgccgcatt   2040
gcatcagcca tgatggatac tttctcggca ggagcaaggt gagatgacag gagatcctgc   2100
```

```
cccggcactt cgcccaatag cagccagtcc cttcccgctt cagtgacaac gtcgagcaca   2160
gctgcgcaag gaacgcccgt cgtggccagc cacgatagcc gcgctgcctc gtcctgcagt   2220
tcattcaggg caccggacag gtcggtcttg acaaaaagaa ccgggcgccc ctgcgctgac   2280
agccggaaca cggcggcatc agagcagccg attgtcagtt gtgcccagtc atagccgaat   2340
agcctctcca cccaagcggc cggagaacct gcgtgcaatc catcttgttc aatcatactc   2400
ttcctttttc aatattattg aagcatttat cagggttatt gtctcatgac caaaatccct   2460
taacgtgagt tttcgttcca ctgagcgtca gaccccgtag aaaagatcaa aggatcttct   2520
tgagatcctt tttttctgcg cgtaatctgc tgcttgcaaa caaaaaaacc accgctacca   2580
gcggtggttt gtttgccgga tcaagagcta ccaactcttt ttccgaaggt aactggcttc   2640
agcagagcgc agataccaaa tactgtcctt ctagtgtagc cgtagttagg ccaccacttc   2700
aagaactctg tagcaccgcc tacatacctc gctctgctaa tcctgttacc agtggctgct   2760
gccagtggcg ataagtcgtg tcttaccggg ttggactcaa gacgatagtt accggataag   2820
gcgcagcggt cgggctgaac ggggggttcg tgcacacagc ccagcttgga gcgaacgacc   2880
tacaccgaac tgagatacct acagcgtgag ctatgagaaa gcgccacgct tcccgaaggg   2940
agaaaggcgg acaggtatcc ggtaagcggc agggtcggaa caggagagcg cacgagggag   3000
cttccagggg gaaacgcctg gtatctttat agtcctgtcg ggtttcgcca cctctgactt   3060
gagcgtcgat ttttgtgatg ctcgtcaggg gggcggagcc tatggaaaaa cgccagcaac   3120
gcggcctttt tacggttcct ggccttttgc tggccttttg ctcacatgtt ctttcctgcg   3180
ttatcccctg attctgtgga taaccgtatt accgcctttg agtgagctga taccgctcgc   3240
cgcagccgaa cgaccgagcg cagcgagtca gtgagcgagg aagcggaaga gcgcctgatg   3300
cggtattttc tccttacgca tctgtgcggt atttcacacc gcatatggtg cactctcagt   3360
acaatctgct ctgatgccgc atagttaagc cagtatacac tccgctatcg ctacgtgact   3420
gggtcatggc tgcgccccga cacccgccaa cacccgctga cgcgccctga cgggcttgtc   3480
tgctcccggc atccgcttac agacaagctg tgaccgtctc cgggagctgc atgtgtcaga   3540
ggttttcacc gtcatcaccg aaacgcgcga ggcagcagat caattcgcgc gcgaaggcga   3600
agcggcatgc ataatgtgcc tgtcaaatgg acgaagcagg gattctgcaa accctatgct   3660
actccgtcaa gccgtcaatt gtctgattcg ttaccaatta tgacaacttg acggctacat   3720
cattcacttt ttcttcacaa ccggcacgga actcgctcgg gctggccccg gtgcattttt   3780
taaatacccg cgagaaatag agttgatcgt caaaaccaac attgcgaccg acggtggcga   3840
taggcatccg ggtggtgctc aaaagcagct tcgcctggct gatacgttgg tcctcgcgcc   3900
agcttaagac gctaatccct aactgctggc ggaaaagatg tgacagacgc gacggcgaca   3960
agcaaacatg ctgtgcgacg ctggcgatat caaaattgct gtctgccagg tgatcgctga   4020
tgtactgaca agcctcgcgt acccgattat ccatcggtgg atggagcgac tcgttaatcg   4080
cttccatgcg ccgcagtaac aattgctcaa gcagatttat cgccagcagc tccgaatagc   4140
gcccttcccc ttgcccggcg ttaatgattt gcccaaacag gtcgctgaaa tgcggctggt   4200
gcgcttcatc cgggcgaaag aaccccgtat tggcaaatat tgacggccag ttaagccatt   4260
catgccagta ggcgcgcgga cgaaagtaaa cccactggtg ataccattcg cgagcctccg   4320
gatgacgacc gtagtgatga atctctcctg gcgggaacag caaaatatca cccggtcggc   4380
aaacaaattc tcgtccctga tttttcacca ccccctgacc gcgaatggtg agattgagaa   4440
tataaccttt cattcccagc ggtcggtcga taaaaaaatc gagataaccg ttggcctcaa   4500
```

tcggcgttaa acccgccacc agatgggcat taaacgagta tcccggcagc aggggatcat 4560
tttgcgcttc agccatactt ttcatactcc cgccattcag ag 4602

<210> SEQ ID NO 20
<211> LENGTH: 4602
<212> TYPE: DNA
<213> ORGANISM: Artificial sequence
<220> FEATURE:
<223> OTHER INFORMATION: Expression plasmid for antibacterial protein AP-4

<400> SEQUENCE: 20
aagaaaccaa ttgtccatat tgcatcagac attgccgtca ctgcgtcttt tactggctct 60
tctcgctaac caaaccggta accccgctta ttaaaagcat tctgtaacaa agcgggacca 120
aagccatgac aaaaacgcgt aacaaaagtg tctataatca cggcagaaaa gtccacattg 180
attatttgca cggcgtcaca ctttgctatg ccatagcatt tttatccata agattagcgg 240
atcctacctg acgcttttta tcgcaactct ctactgtttc tccatacccg tttttttggg 300
ctagaaataa ttttgtttaa ctttaagaag gagatataca tatggcaatg tcaccggcac 360
tacgaaatag cgtaatagcg gcgataagtg gcggggctat tgccatagca tctgtgttaa 420
tcactggccc cggtggtaac gatggtctgg aaggtgtcag acacaaacca tacaaggacg 480
tagttggtgt gttgactgtg tgttatggcc acgtcggaaa agacatcatg ctcggtaaaa 540
cgtataccga agcagaatgc aaagccctcc tgaataaaga ccttgccacg gtcgccagac 600
aaattaaccc gtacatcaaa gtcaaaatac cggaaacaac gcgcggcgct ctttattcgt 660
tcgtctataa cgtgggcgca ggcaatttca gaacatcgac gcttcttcgc aaaatcaacc 720
agggcgatat caagggcgca tgtgaccagc tacgtcgctg gacatacgct ggcggtaagc 780
aatggaaagg gctgatgact cgccgtgaga ttgagcgtga agtctgtttg tgggggcagc 840
aaggcggagg gggctcgctg atggatctgg cggattaagc ggccgcaagg gcgagcttga 900
aggtaagcct atccctaacc ctctcctcgg tctcgattct acgcgtaccg gtcatcatca 960
ccatcaccat tgagtttaaa cggtctccag cttggctgtt ttggcggatg agagaagatt 1020
ttcagcctga tacagattaa atcagaacgc agaagcggtc tgataaaaca gaatttgcct 1080
ggcggcagta gcgcggtggt cccacctgac cccatgccga actcagaagt gaaacgccgt 1140
agcgccgatg gtagtgtggg gtctccccat gcgagagtag ggaactgcca ggcatcaaat 1200
aaaacgaaag gctcagtcga aagactgggc ctttcgtttt atctgttgtt tgtcggtgaa 1260
cgctctcctg agtaggacaa atccgccggg agcggatttg aacgttgcga agcaacggcc 1320
cggagggtgg cgggcaggac gcccgccata aactgccagg catcaaatta agcagaaggc 1380
catcctgacg gatggccttt ttgcgtttct acaaactctt ttgtttattt ttctaaatac 1440
attcaaatat gtatccgctc atgagattat caaaaaggat cttcacctag atccttttaa 1500
attaaaaatg aagttttaaa tcaatctaaa gtatatatga gtaaacttgg tctgacagtt 1560
aggcgtcgct tggtcggtca tttcgaaccc cagagtcccg ctcagaagaa ctcgtcaaga 1620
aggcgataga aggcgatgcg ctgcgaatcg ggagcggcga taccgtaaag cacgaggaag 1680
cggtcagccc attcgccgcc aagctcttca gcaatatcac gggtagccaa cgctatgtcc 1740
tgatagcggt ccgccacacc cagccggcca cagtcgatga atccagaaaa gcggccattt 1800
tccaccatga tattcggcaa gcaggcatcg ccatgtgtca cgacgagatc ctcgccgtcg 1860
ggcatgcgcg ccttgagcct ggcgaacagt tcggctggcg cgagcccctg atgctcttcg 1920

```
tccagatcat cctgatcgac aagaccggct tccatccgag tacgtgctcg ctcgatgcga   1980
tgtttcgctt ggtggtcgaa tgggcaggta gccggatcaa gcgtatgcag ccgccgcatt   2040
gcatcagcca tgatggatac tttctcggca ggagcaaggt gagatgacag gagatcctgc   2100
cccggcactt cgcccaatag cagccagtcc cttcccgctt cagtgacaac gtcgagcaca   2160
gctgcgcaag gaacgcccgt cgtggccagc cacgatagcc gcgctgcctc gtcctgcagt   2220
tcattcaggg caccggacag gtcggtcttg acaaaaagaa ccgggcgccc ctgcgctgac   2280
agccggaaca cggcggcatc agagcagccg attgtcagtt gtgcccagtc atagccgaat   2340
agcctctcca cccaagcggc cggagaacct gcgtgcaatc catcttgttc aatcatactc   2400
ttcctttttc aatattattg aagcatttat cagggttatt gtctcatgac caaaatccct   2460
taacgtgagt tttcgttcca ctgagcgtca gaccccgtag aaaagatcaa aggatcttct   2520
tgagatcctt tttttctgcg cgtaatctgc tgcttgcaaa caaaaaaacc accgctacca   2580
gcggtggttt gtttgccgga tcaagagcta ccaactcttt ttccgaaggt aactggcttc   2640
agcagagcgc agataccaaa tactgtcctt ctagtgtagc cgtagttagg ccaccacttc   2700
aagaactctg tagcaccgcc tacatacctc gctctgctaa tcctgttacc agtggctgct   2760
gccagtggcg ataagtcgtg tcttaccggg ttggactcaa gacgatagtt accggataag   2820
gcgcagcggt cgggctgaac ggggggttcg tgcacacagc ccagcttgga gcgaacgacc   2880
tacaccgaac tgagatacct acagcgtgag ctatgagaaa gcgccacgct tcccgaaggg   2940
agaaaggcgg acaggtatcc ggtaagcggc agggtcggaa caggagagcg cacgagggag   3000
cttccagggg gaaacgcctg gtatctttat agtcctgtcg ggtttcgcca cctctgactt   3060
gagcgtcgat ttttgtgatg ctcgtcaggg gggcggagcc tatggaaaaa cgccagcaac   3120
gcggcctttt tacggttcct ggccttttgc tggccttttg ctcacatgtt ctttcctgcg   3180
ttatcccctg attctgtgga taaccgtatt accgcctttg agtgagctga taccgctcgc   3240
cgcagccgaa cgaccgagcg cagcgagtca gtgagcgagg aagcggaaga gcgcctgatg   3300
cggtattttc tccttacgca tctgtgcggt atttcacacc gcatatggtg cactctcagt   3360
acaatctgct ctgatgccgc atagttaagc cagtatacac tccgctatcg ctacgtgact   3420
gggtcatggc tgcgccccga cacccgccaa cacccgctga cgcgccctga cgggcttgtc   3480
tgctcccggc atccgcttac agacaagctg tgaccgtctc cgggagctgc atgtgtcaga   3540
ggttttcacc gtcatcaccg aaacgcgcga ggcagcagat caattcgcgc gcgaaggcga   3600
agcggcatgc ataatgtgcc tgtcaaatgg acgaagcagg gattctgcaa accctatgct   3660
actccgtcaa gccgtcaatt gtctgattcg ttaccaatta tgacaacttg acggctacat   3720
cattcacttt ttcttcacaa ccggcacgga actcgctcgg gctggccccg gtgcattttt   3780
taaatacccg cgagaaatag agttgatcgt caaaaccaac attgcgaccg acggtggcga   3840
taggcatccg ggtggtgctc aaaagcagct tcgcctggct gatacgttgg tcctcgcgcc   3900
agcttaagac gctaatccct aactgctggc ggaaaagatg tgacagacgc gacggcgaca   3960
agcaaacatg ctgtgcgacg ctggcgatat caaaattgct gtctgccagg tgatcgctga   4020
tgtactgaca agcctcgcgt acccgattat ccatcggtgg atggagcgac tcgttaatcg   4080
cttccatgcg ccgcagtaac aattgctcaa gcagatttat cgccagcagc tccgaatagc   4140
gcccttcccc ttgcccggcg ttaatgattt gcccaaacag gtcgctgaaa tgcggctggt   4200
gcgcttcatc cgggcgaaag aaccccgtat tggcaaatat tgacggccag ttaagccatt   4260
catgccagta ggcgcgcgga cgaaagtaaa cccactggtg ataccattcg cgagcctccg   4320
```

```
gatgacgacc gtagtgatga atctctcctg gcgggaacag caaaatatca cccggtcggc   4380

aaacaaattc tcgtccctga tttttcacca ccccctgacc gcgaatggtg agattgagaa   4440

tataaccttt cattcccagc ggtcggtcga taaaaaaatc gagataaccg ttggcctcaa   4500

tcggcgttaa acccgccacc agatgggcat taaacgagta tcccggcagc aggggatcat   4560

tttgcgcttc agccatactt ttcatactcc cgccattcag ag                      4602
```

<210> SEQ ID NO 21
<211> LENGTH: 4602
<212> TYPE: DNA
<213> ORGANISM: Artificial sequence
<220> FEATURE:
<223> OTHER INFORMATION: Expression plasmid for antibacterial protein AP-5

<400> SEQUENCE: 21

```
aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttttggg    300

ctagaaataa ttttgtttaa ctttaagaag gagatataca tatggcaatg tcaccggcac    360

tacgaaaaag cgtaatagcg gcgataagtg gcggggctat tgccatagca tctgtgttaa    420

tcactggccc cggtggtaac gatggtctgg aaggtgtcag acacaaacca tacaaggacg    480

tagttggtgt gttgactgtg tgtcatggcc acgtcggaaa agacatcatg ctcggtaaaa    540

cgtataccga agcagaatgc aaagccctcc tgaataaaga ccttgccacg gtcgccagac    600

aaattaaccc gtacatcaaa gtcgatatac cggaaacaac gcgcggcgct ctttattcgt    660

tcgtctataa cgtgggcgca ggcaatttca gaacatcgac gcttcttcgc aaaatcaacc    720

agggcgatat caagggcgca tgtgaccagc tacgtcgctg gacatacgct ggcggtaagc    780

aatggaaagg gctgatgact cgccgtgaga ttgagcgtga agtctgtttg tgggggcagc    840

aaggcggagg gggctcgctg atggatctgg cggattaagc ggccgcaagg gcgagcttga    900

aggtaagcct atccctaacc ctctcctcgg tctcgattct acgcgtaccg gtcatcatca    960

ccatcaccat tgagtttaaa cggtctccag cttggctgtt ttggcggatg agagaagatt   1020

ttcagcctga tacagattaa atcagaacgc agaagcggtc tgataaaaca gaatttgcct   1080

ggcggcagta gcgcggtggt cccacctgac cccatgccga actcagaagt gaaacgccgt   1140

agcgccgatg gtagtgtggg gtctccccat gcgagagtag ggaactgcca ggcatcaaat   1200

aaaacgaaag gctcagtcga aagactgggc ctttcgtttt atctgttgtt tgtcggtgaa   1260

cgctctcctg agtaggacaa atccgccggg agcggatttg aacgttgcga agcaacggcc   1320

cggagggtgg cgggcaggac gcccgccata aactgccagg catcaaatta agcagaaggc   1380

catcctgacg gatggccttt ttgcgtttct acaaactctt ttgtttattt ttctaaatac   1440

attcaaatat gtatccgctc atgagattat caaaaaggat cttcacctag atccttttaa   1500

attaaaaatg aagttttaaa tcaatctaaa gtatatatga gtaaacttgg tctgacagtt   1560

aggcgtcgct tggtcggtca tttcgaaccc cagagtcccg ctcagaagaa ctcgtcaaga   1620

aggcgataga aggcgatgcg ctgcgaatcg ggagcggcga taccgtaaag cacgaggaag   1680

cggtcagccc attcgccgcc aagctcttca gcaatatcac gggtagccaa cgctatgtcc   1740
```

-continued

```
tgatagcggt ccgccacacc cagccggcca cagtcgatga atccagaaaa gcggccattt   1800
tccaccatga tattcggcaa gcaggcatcg ccatgtgtca cgacgagatc ctcgccgtcg   1860
ggcatgcgcg ccttgagcct ggcgaacagt tcggctggcg cgagcccctg atgctcttcg   1920
tccagatcat cctgatcgac aagaccggct tccatccgag tacgtgctcg ctcgatgcga   1980
tgtttcgctt ggtggtcgaa tgggcaggta gccggatcaa gcgtatgcag ccgccgcatt   2040
gcatcagcca tgatggatac tttctcggca ggagcaaggt gagatgacag gagatcctgc   2100
cccggcactt cgcccaatag cagccagtcc cttcccgctt cagtgacaac gtcgagcaca   2160
gctgcgcaag gaacgcccgt cgtggccagc cacgatagcc gcgctgcctc gtcctgcagt   2220
tcattcaggg caccggacag gtcggtcttg acaaaaagaa ccgggcgccc ctgcgctgac   2280
agccggaaca cggcggcatc agagcagccg attgtcagtt gtgcccagtc atagccgaat   2340
agcctctcca cccaagcggc cggagaacct gcgtgcaatc catcttgttc aatcatactc   2400
ttcctttttc aatattattg aagcatttat cagggttatt gtctcatgac caaaatccct   2460
taacgtgagt tttcgttcca ctgagcgtca gaccccgtag aaaagatcaa aggatcttct   2520
tgagatcctt tttttctgcg cgtaatctgc tgcttgcaaa caaaaaaacc accgctacca   2580
gcggtggttt gtttgccgga tcaagagcta ccaactcttt ttccgaaggt aactggcttc   2640
agcagagcgc agataccaaa tactgtcctt ctagtgtagc cgtagttagg ccaccacttc   2700
aagaactctg tagcaccgcc tacatacctc gctctgctaa tcctgttacc agtggctgct   2760
gccagtggcg ataagtcgtg tcttaccggg ttggactcaa gacgatagtt accggataag   2820
gcgcagcggt cgggctgaac ggggggttcg tgcacacagc ccagcttgga gcgaacgacc   2880
tacaccgaac tgagatacct acagcgtgag ctatgagaaa gcgccacgct tcccgaaggg   2940
agaaaggcgg acaggtatcc ggtaagcggc agggtcggaa caggagagcg cacgagggag   3000
cttccagggg gaaacgcctg gtatctttat agtcctgtcg ggtttcgcca cctctgactt   3060
gagcgtcgat ttttgtgatg ctcgtcaggg gggcggagcc tatggaaaaa cgccagcaac   3120
gcggcctttt tacggttcct ggccttttgc tggccttttg ctcacatgtt ctttcctgcg   3180
ttatcccctg attctgtgga taaccgtatt accgcctttg agtgagctga taccgctcgc   3240
cgcagccgaa cgaccgagcg cagcgagtca gtgagcgagg aagcggaaga gcgcctgatg   3300
cggtattttc tccttacgca tctgtgcggt atttcacacc gcatatggtg cactctcagt   3360
acaatctgct ctgatgccgc atagttaagc cagtatacac tccgctatcg ctacgtgact   3420
gggtcatggc tgcgccccga cacccgccaa cacccgctga cgcgccctga cgggcttgtc   3480
tgctcccggc atccgcttac agacaagctg tgaccgtctc cgggagctgc atgtgtcaga   3540
ggttttcacc gtcatcaccg aaacgcgcga ggcagcagat caattcgcgc gcgaaggcga   3600
agcggcatgc ataatgtgcc tgtcaaatgg acgaagcagg gattctgcaa accctatgct   3660
actccgtcaa gccgtcaatt gtctgattcg ttaccaatta tgacaacttg acggctacat   3720
cattcacttt ttcttcacaa ccggcacgga actcgctcgg gctggccccg gtgcattttt   3780
taaatacccg cgagaaatag agttgatcgt caaaaccaac attgcgaccg acggtggcga   3840
taggcatccg ggtggtgctc aaaagcagct tcgcctggct gatacgttgg tcctcgcgcc   3900
agcttaagac gctaatccct aactgctggc ggaaaagatg tgacagacgc gacggcgaca   3960
agcaaacatg ctgtgcgacg ctggcgatat caaaattgct gtctgccagg tgatcgctga   4020
tgtactgaca agcctcgcgt acccgattat ccatcggtgg atggagcgac tcgttaatcg   4080
cttccatgcg ccgcagtaac aattgctcaa gcagatttat cgccagcagc tccgaatagc   4140
```

```
gcccttcccc ttgcccggcg ttaatgattt gcccaaacag gtcgctgaaa tgcggctggt   4200

gcgcttcatc cgggcgaaag aaccccgtat tggcaaatat tgacggccag ttaagccatt   4260

catgccagta ggcgcgcgga cgaaagtaaa cccactggtg ataccattcg cgagcctccg   4320

gatgacgacc gtagtgatga atctctcctg gcgggaacag caaaatatca cccggtcggc   4380

aaacaaattc tcgtccctga tttttcacca ccccctgacc gcgaatggtg agattgagaa   4440

tataaccttt cattcccagc ggtcggtcga taaaaaaatc gagataaccg ttggcctcaa   4500

tcggcgttaa acccgccacc agatgggcat taaacgagta tcccggcagc aggggatcat   4560

tttgcgcttc agccatactt ttcatactcc cgccattcag ag                      4602
```

<210> SEQ ID NO 22
<211> LENGTH: 4602
<212> TYPE: DNA
<213> ORGANISM: Artificial sequence
<220> FEATURE:
<223> OTHER INFORMATION: Expression plasmid for antibacterial protein AP-6

<400> SEQUENCE: 22

```
aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttttggg    300

ctagaaataa ttttgtttaa ctttaagaag gagatataca tatggcaatg tcaccggcac    360

tacgaaaaag cgtaatagcg gcgataagtg gcggggctat tgccatagca tctgtgttaa    420

tcactggccc cggtggtaac gatggtctgg aaggtgtcag acacaaacca tacaaggacg    480

tagttggtgt gttgactgtg tgttatggcc acgtcggaaa agacatcatg ctcggtaaaa    540

cgtataccga agcagaatgc aaagccctcc tgaataaaga ccttgccacg gtcgccagac    600

aaattaaccc gtacatcaaa gtcaaaatac cggaaacaac gcgcggcgct ctttattcgt    660

tcgtctataa cgtgggcgca ggcaatttca gaacatcgac gcttcttcgc aaaatcaacc    720

agggcgatat caagggcgca tgtgaccagc tacgtcgctg gacatacgct ggcggtaagc    780

aatggaaagg gctgatgact cgccgtgaga ttgagcgtga agtctgtttg tgggggcagc    840

aaggcggagg gggctcgctg atggatctgg cggattaagc ggccgcaagg gcgagcttga    900

aggtaagcct atccctaacc ctctcctcgg tctcgattct acgcgtaccg gtcatcatca    960

ccatcaccat tgagtttaaa cggtctccag cttggctgtt ttggcggatg agagaagatt   1020

ttcagcctga tacagattaa atcagaacgc agaagcggtc tgataaaaca gaatttgcct   1080

ggcggcagta gcgcggtggt cccacctgac cccatgccga actcagaagt gaaacgccgt   1140

agcgccgatg gtagtgtggg gtctccccat gcgagagtag ggaactgcca ggcatcaaat   1200

aaaacgaaag gctcagtcga aagactgggc ctttcgtttt atctgttgtt tgtcggtgaa   1260

cgctctcctg agtaggacaa atccgccggg agcggatttg aacgttgcga agcaacggcc   1320

cggagggtgg cgggcaggac gcccgccata aactgccagg catcaaatta agcagaaggc   1380

catcctgacg gatggccttt ttgcgtttct acaaactctt ttgtttattt ttctaaatac   1440

attcaaatat gtatccgctc atgagattat caaaaaggat cttcacctag atccttttaa   1500

attaaaaatg aagttttaaa tcaatctaaa gtatatatga gtaaacttgg tctgacagtt   1560
```

-continued aggcgtcgct tggtcggtca tttcgaaccc cagagtcccg ctcagaagaa ctcgtcaaga 1620
aggcgataga aggcgatgcg ctgcgaatcg ggagcggcga taccgtaaag cacgaggaag 1680
cggtcagccc attcgccgcc aagctcttca gcaatatcac gggtagccaa cgctatgtcc 1740
tgatagcggt ccgccacacc cagccggcca cagtcgatga atccagaaaa gcggccattt 1800
tccaccatga tattcggcaa gcaggcatcg ccatgtgtca cgacgagatc ctcgccgtcg 1860
ggcatgcgcg ccttgagcct ggcgaacagt tcggctggcg cgagcccctg atgctcttcg 1920
tccagatcat cctgatcgac aagaccggct tccatccgag tacgtgctcg ctcgatgcga 1980
tgtttcgctt ggtggtcgaa tgggcaggta gccggatcaa gcgtatgcag ccgccgcatt 2040
gcatcagcca tgatggatac tttctcggca ggagcaaggt gagatgacag gagatcctgc 2100
cccggcactt cgcccaatag cagccagtcc cttcccgctt cagtgacaac gtcgagcaca 2160
gctgcgcaag gaacgcccgt cgtggccagc cacgatagcc gcgctgcctc gtcctgcagt 2220
tcattcaggg caccggacag gtcggtcttg acaaaaagaa ccgggcgccc ctgcgctgac 2280
agccggaaca cggcggcatc agagcagccg attgtcagtt gtgcccagtc atagccgaat 2340
agcctctcca cccaagcggc cggagaacct gcgtgcaatc catcttgttc aatcatactc 2400
ttcctttttc aatattattg aagcatttat cagggttatt gtctcatgac caaaatccct 2460
taacgtgagt tttcgttcca ctgagcgtca gaccccgtag aaaagatcaa aggatcttct 2520
tgagatcctt tttttctgcg cgtaatctgc tgcttgcaaa caaaaaaacc accgctacca 2580
gcggtggttt gtttgccgga tcaagagcta ccaactcttt ttccgaaggt aactggcttc 2640
agcagagcgc agataccaaa tactgtcctt ctagtgtagc cgtagttagg ccaccacttc 2700
aagaactctg tagcaccgcc tacatacctc gctctgctaa tcctgttacc agtggctgct 2760
gccagtggcg ataagtcgtg tcttaccggg ttggactcaa gacgatagtt accggataag 2820
gcgcagcggt cgggctgaac ggggggttcg tgcacacagc ccagcttgga gcgaacgacc 2880
tacaccgaac tgagatacct acagcgtgag ctatgagaaa gcgccacgct tcccgaaggg 2940
agaaaggcgg acaggtatcc ggtaagcggc agggtcggaa caggagagcg cacgagggag 3000
cttccagggg gaaacgcctg gtatctttat agtcctgtcg ggtttcgcca cctctgactt 3060
gagcgtcgat ttttgtgatg ctcgtcaggg gggcggagcc tatggaaaaa cgccagcaac 3120
gcggcctttt tacggttcct ggccttttgc tggccttttg ctcacatgtt ctttcctgcg 3180
ttatcccctg attctgtgga taaccgtatt accgcctttg agtgagctga taccgctcgc 3240
cgcagccgaa cgaccgagcg cagcgagtca gtgagcgagg aagcggaaga gcgcctgatg 3300
cggtattttc tccttacgca tctgtgcggt atttcacacc gcatatggtg cactctcagt 3360
acaatctgct ctgatgccgc atagttaagc cagtatacac tccgctatcg ctacgtgact 3420
gggtcatggc tgcgccccga cacccgccaa cacccgctga cgcgccctga cgggcttgtc 3480
tgctcccggc atccgcttac agacaagctg tgaccgtctc cgggagctgc atgtgtcaga 3540
ggttttcacc gtcatcaccg aaacgcgcga ggcagcagat caattcgcgc gcgaaggcga 3600
agcggcatgc ataatgtgcc tgtcaaatgg acgaagcagg gattctgcaa accctatgct 3660
actccgtcaa gccgtcaatt gtctgattcg ttaccaatta tgacaacttg acggctacat 3720
cattcacttt ttcttcacaa ccggcacgga actcgctcgg gctggccccg gtgcattttt 3780
taaatacccg cgagaaatag agttgatcgt caaaaccaac attgcgaccg acggtggcga 3840
taggcatccg ggtggtgctc aaaagcagct tcgcctggct gatacgttgg tcctcgcgcc 3900
agcttaagac gctaatccct aactgctggc ggaaaagatg tgacagacgc gacggcgaca 3960

```
agcaaacatg ctgtgcgacg ctggcgatat caaaattgct gtctgccagg tgatcgctga   4020

tgtactgaca agcctcgcgt acccgattat ccatcggtgg atggagcgac tcgttaatcg   4080

cttccatgcg ccgcagtaac aattgctcaa gcagatttat cgccagcagc tccgaatagc   4140

gcccttcccc ttgcccggcg ttaatgattt gcccaaacag gtcgctgaaa tgcggctggt   4200

gcgcttcatc cgggcgaaag aaccccgtat tggcaaatat tgacggccag ttaagccatt   4260

catgccagta ggcgcgcgga cgaaagtaaa cccactggtg ataccattcg cgagcctccg   4320

gatgacgacc gtagtgatga atctctcctg gcgggaacag caaaatatca cccggtcggc   4380

aaacaaattc tcgtccctga tttttcacca ccccctgacc gcgaatggtg agattgagaa   4440

tataaccttt cattcccagc ggtcggtcga taaaaaaatc gagataaccg ttggcctcaa   4500

tcggcgttaa acccgccacc agatgggcat taaacgagta tcccggcagc aggggatcat   4560

tttgcgcttc agccatactt ttcatactcc cgccattcag ag                      4602
```

```
<210> SEQ ID NO 23
<211> LENGTH: 4602
<212> TYPE: DNA
<213> ORGANISM: Artificial sequence
<220> FEATURE:
<223> OTHER INFORMATION: Expression plasmid for antibacterial protein
      AP-7

<400> SEQUENCE: 23

aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttttggg    300

ctagaaataa ttttgtttaa ctttaagaag gagatataca tatggcaatg tcaccggcac    360

tacgaaatag cgtaatagcg gcgataagtg gcggggctat tgccatagca tctgtgttaa    420

tcactggccc cggtggtaac gatggtctgg aaggtgtcag acacaaacca tacaaggacg    480

tagttggtgt gttgactgtg tgtcatggcc acgtcggaaa agacatcatg ctcggtaaaa    540

cgtataccga agcagaatgc aaagccctcc tgaataaaga ccttgccacg gtcgccagac    600

aaattaaccc gtacatcaaa gtcaaaatac cggaaacaac gcgcggcgct ctttattcgt    660

tcgtctataa cgtgggcgca ggcaatttca gaacatcgac gcttcttcgc aaaatcaacc    720

agggcgatat caagggcgca tgtgaccagc tacgtcgctg gacatacgct ggcggtaagc    780

aatggaaagg gctgatgact cgccgtgaga ttgagcgtga agtctgtttg tgggggcagc    840

aaggcggagg gggctcgctg atggatctgg cggattaagc ggccgcaagg gcgagcttga    900

aggtaagcct atccctaacc ctctcctcgg tctcgattct acgcgtaccg gtcatcatca    960

ccatcaccat tgagtttaaa cggtctccag cttggctgtt ttggcggatg agagaagatt   1020

ttcagcctga tacagattaa atcagaacgc agaagcggtc tgataaaaca gaatttgcct   1080

ggcggcagta gcgcggtggt cccacctgac cccatgccga actcagaagt gaaacgccgt   1140

agcgccgatg gtagtgtggg gtctccccat gcgagagtag ggaactgcca ggcatcaaat   1200

aaaacgaaag gctcagtcga aagactgggc ctttcgtttt atctgttgtt tgtcggtgaa   1260

cgctctcctg agtaggacaa atccgccggg agcggatttg aacgttgcga agcaacggcc   1320

cggagggtgg cgggcaggac gcccgccata aactgccagg catcaaatta agcagaaggc   1380
```

```
catcctgacg gatggccttt ttgcgtttct acaaactctt ttgtttattt ttctaaatac   1440
attcaaatat gtatccgctc atgagattat caaaaaggat cttcacctag atccttttaa   1500
attaaaaatg aagttttaaa tcaatctaaa gtatatatga gtaaacttgg tctgacagtt   1560
aggcgtcgct tggtcggtca tttcgaaccc cagagtcccg ctcagaagaa ctcgtcaaga   1620
aggcgataga aggcgatgcg ctgcgaatcg ggagcggcga taccgtaaag cacgaggaag   1680
cggtcagccc attcgccgcc aagctcttca gcaatatcac gggtagccaa cgctatgtcc   1740
tgatagcggt ccgccacacc cagccggcca cagtcgatga atccagaaaa gcggccattt   1800
tccaccatga tattcggcaa gcaggcatcg ccatgtgtca cgacgagatc ctcgccgtcg   1860
ggcatgcgcg ccttgagcct ggcgaacagt tcggctggcg cgagcccctg atgctcttcg   1920
tccagatcat cctgatcgac aagaccggct tccatccgag tacgtgctcg ctcgatgcga   1980
tgtttcgctt ggtggtcgaa tgggcaggta gccggatcaa gcgtatgcag ccgccgcatt   2040
gcatcagcca tgatggatac tttctcggca ggagcaaggt gagatgacag gagatcctgc   2100
cccggcactt cgcccaatag cagccagtcc cttcccgctt cagtgacaac gtcgagcaca   2160
gctgcgcaag gaacgcccgt cgtggccagc cacgatagcc gcgctgcctc gtcctgcagt   2220
tcattcaggg caccggacag gtcggtcttg acaaaaagaa ccgggcgccc ctgcgctgac   2280
agccggaaca cggcggcatc agagcagccg attgtcagtt gtgcccagtc atagccgaat   2340
agcctctcca cccaagcggc cggagaacct gcgtgcaatc catcttgttc aatcatactc   2400
ttcctttttc aatattattg aagcatttat cagggttatt gtctcatgac caaaatccct   2460
taacgtgagt tttcgttcca ctgagcgtca gaccccgtag aaaagatcaa aggatcttct   2520
tgagatcctt tttttctgcg cgtaatctgc tgcttgcaaa caaaaaaacc accgctacca   2580
gcggtggttt gtttgccgga tcaagagcta ccaactcttt ttccgaaggt aactggcttc   2640
agcagagcgc agataccaaa tactgtcctt ctagtgtagc cgtagttagg ccaccacttc   2700
aagaactctg tagcaccgcc tacatacctc gctctgctaa tcctgttacc agtggctgct   2760
gccagtggcg ataagtcgtg tcttaccggg ttggactcaa gacgatagtt accggataag   2820
gcgcagcggt cgggctgaac ggggggttcg tgcacacagc ccagcttgga gcgaacgacc   2880
tacaccgaac tgagatacct acagcgtgag ctatgagaaa gcgccacgct tcccgaaggg   2940
agaaaggcgg acaggtatcc ggtaagcggc agggtcggaa caggagagcg cacgagggag   3000
cttccagggg gaaacgcctg gtatctttat agtcctgtcg ggtttcgcca cctctgactt   3060
gagcgtcgat ttttgtgatg ctcgtcaggg gggcggagcc tatggaaaaa cgccagcaac   3120
gcggcctttt tacggttcct ggccttttgc tggccttttg ctcacatgtt ctttcctgcg   3180
ttatcccctg attctgtgga taaccgtatt accgcctttg agtgagctga taccgctcgc   3240
cgcagccgaa cgaccgagcg cagcgagtca gtgagcgagg aagcggaaga gcgcctgatg   3300
cggtattttc tccttacgca tctgtgcggt atttcacacc gcatatggtg cactctcagt   3360
acaatctgct ctgatgccgc atagttaagc cagtatacac tccgctatcg ctacgtgact   3420
gggtcatggc tgcgccccga cacccgccaa cacccgctga cgcgccctga cgggcttgtc   3480
tgctcccggc atccgcttac agacaagctg tgaccgtctc cgggagctgc atgtgtcaga   3540
ggttttcacc gtcatcaccg aaacgcgcga ggcagcagat caattcgcgc gcgaaggcga   3600
agcggcatgc ataatgtgcc tgtcaaatgg acgaagcagg gattctgcaa accctatgct   3660
actccgtcaa gccgtcaatt gtctgattcg ttaccaatta tgacaacttg acggctacat   3720
cattcacttt ttcttcacaa ccggcacgga actcgctcgg gctggccccg gtgcattttt   3780
```

```
taaatacccg cgagaaatag agttgatcgt caaaaccaac attgcgaccg acggtggcga   3840

taggcatccg ggtggtgctc aaaagcagct tcgcctggct gatacgttgg tcctcgcgcc   3900

agcttaagac gctaatccct aactgctggc ggaaaagatg tgacagacgc gacggcgaca   3960

agcaaacatg ctgtgcgacg ctggcgatat caaaattgct gtctgccagg tgatcgctga   4020

tgtactgaca agcctcgcgt acccgattat ccatcggtgg atggagcgac tcgttaatcg   4080

cttccatgcg ccgcagtaac aattgctcaa gcagatttat cgccagcagc tccgaatagc   4140

gcccttcccc ttgcccggcg ttaatgattt gcccaaacag gtcgctgaaa tgcggctggt   4200

gcgcttcatc cgggcgaaag aaccccgtat tggcaaatat tgacggccag ttaagccatt   4260

catgccagta ggcgcgcgga cgaaagtaaa cccactggtg ataccattcg cgagcctccg   4320

gatgacgacc gtagtgatga atctctcctg gcgggaacag caaaatatca cccggtcggc   4380

aaacaaattc tcgtccctga tttttcacca ccccctgacc gcgaatggtg agattgagaa   4440

tataaccttt cattcccagc ggtcggtcga taaaaaaatc gagataaccg ttggcctcaa   4500

tcggcgttaa acccgccacc agatgggcat taaacgagta tcccggcagc aggggatcat   4560

tttgcgcttc agccatactt ttcatactcc cgccattcag ag                      4602
```

<210> SEQ ID NO 24
<211> LENGTH: 4602
<212> TYPE: DNA
<213> ORGANISM: Artificial sequence
<220> FEATURE:
<223> OTHER INFORMATION: Expression plasmid for antibacterial protein AP-8

<400> SEQUENCE: 24

```
aagaaaccaa ttgtccatat tgcatcagac attgccgtca ctgcgtcttt tactggctct     60

tctcgctaac caaaccggta accccgctta ttaaaagcat tctgtaacaa agcgggacca    120

aagccatgac aaaaacgcgt aacaaaagtg tctataatca cggcagaaaa gtccacattg    180

attatttgca cggcgtcaca ctttgctatg ccatagcatt tttatccata agattagcgg    240

atcctacctg acgcttttta tcgcaactct ctactgtttc tccatacccg tttttttggg    300

ctagaaataa ttttgtttaa ctttaagaag gagatataca tatggcaatg tcaccggcac    360

tacgaaaaag cgtaatagcg gcgataagtg gcggggctat tgccatagca tctgtgttaa    420

tcactggccc cggtggtaac gatggtctgg aaggtgtcag acacaaacca tacaaggacg    480

tagttggtgt gttgactgtg tgtcatggcc acgtcggaaa agacatcatg ctcggtaaaa    540

cgtataccga agcagaatgc aaagccctcc tgaataaaga ccttgccacg gtcgccagac    600

aaattaaccc gtacatcaaa gtcaaaatac cggaaacaac gcgcggcgct ctttattcgt    660

tcgtctataa cgtgggcgca ggcaatttca gaacatcgac gcttcttcgc aaaatcaacc    720

agggcgatat caagggcgca tgtgaccagc tacgtcgctg gacatacgct ggcggtaagc    780

aatggaaagg gctgatgact cgccgtgaga ttgagcgtga agtctgtttg tgggggcagc    840

aaggcggagg gggctcgctg atggatctgg cggattaagc ggccgcaagg gcgagcttga    900

aggtaagcct atccctaacc ctctcctcgg tctcgattct acgcgtaccg gtcatcatca    960

ccatcaccat tgagtttaaa cggtctccag cttggctgtt ttggcggatg agagaagatt   1020

ttcagcctga tacagattaa atcagaacgc agaagcggtc tgataaaaca gaatttgcct   1080

ggcggcagta gcgcggtggt cccacctgac cccatgccga actcagaagt gaaacgccgt   1140

agcgccgatg gtagtgtggg gtctccccat gcgagagtag ggaactgcca ggcatcaaat   1200
```

```
aaaacgaaag gctcagtcga aagactgggc ctttcgtttt atctgttgtt tgtcggtgaa   1260
cgctctcctg agtaggacaa atccgccggg agcggatttg aacgttgcga agcaacggcc   1320
cggagggtgg cgggcaggac gcccgccata aactgccagg catcaaatta agcagaaggc   1380
catcctgacg gatggccttt ttgcgtttct acaaactctt ttgtttattt ttctaaatac   1440
attcaaatat gtatccgctc atgagattat caaaaaggat cttcacctag atccttttaa   1500
attaaaaatg aagttttaaa tcaatctaaa gtatatatga gtaaacttgg tctgacagtt   1560
aggcgtcgct tggtcggtca tttcgaaccc cagagtcccg ctcagaagaa ctcgtcaaga   1620
aggcgataga aggcgatgcg ctgcgaatcg ggagcggcga taccgtaaag cacgaggaag   1680
cggtcagccc attcgccgcc aagctcttca gcaatatcac gggtagccaa cgctatgtcc   1740
tgatagcggt ccgccacacc cagccggcca cagtcgatga atccagaaaa gcggccattt   1800
tccaccatga tattcggcaa gcaggcatcg ccatgtgtca cgacgagatc ctcgccgtcg   1860
ggcatgcgcg ccttgagcct ggcgaacagt tcggctggcg cgagcccctg atgctcttcg   1920
tccagatcat cctgatcgac aagaccggct tccatccgag tacgtgctcg ctcgatgcga   1980
tgtttcgctt ggtggtcgaa tgggcaggta gccggatcaa gcgtatgcag ccgccgcatt   2040
gcatcagcca tgatggatac tttctcggca ggagcaaggt gagatgacag gagatcctgc   2100
cccggcactt cgcccaatag cagccagtcc cttcccgctt cagtgacaac gtcgagcaca   2160
gctgcgcaag gaacgcccgt cgtggccagc cacgatagcc gcgctgcctc gtcctgcagt   2220
tcattcaggg caccggacag gtcggtcttg acaaaaagaa ccgggcgccc ctgcgctgac   2280
agccggaaca cggcggcatc agagcagccg attgtcagtt gtgcccagtc atagccgaat   2340
agcctctcca cccaagcggc cggagaacct gcgtgcaatc catcttgttc aatcatactc   2400
ttcctttttc aatattattg aagcatttat cagggttatt gtctcatgac caaaatccct   2460
taacgtgagt tttcgttcca ctgagcgtca gaccccgtag aaaagatcaa aggatcttct   2520
tgagatcctt tttttctgcg cgtaatctgc tgcttgcaaa caaaaaaacc accgctacca   2580
gcggtggttt gtttgccgga tcaagagcta ccaactcttt ttccgaaggt aactggcttc   2640
agcagagcgc agataccaaa tactgtcctt ctagtgtagc cgtagttagg ccaccacttc   2700
aagaactctg tagcaccgcc tacatacctc gctctgctaa tcctgttacc agtggctgct   2760
gccagtggcg ataagtcgtg tcttaccggg ttggactcaa gacgatagtt accggataag   2820
gcgcagcggt cgggctgaac ggggggttcg tgcacacagc ccagcttgga gcgaacgacc   2880
tacaccgaac tgagatacct acagcgtgag ctatgagaaa gcgccacgct tcccgaaggg   2940
agaaaggcgg acaggtatcc ggtaagcggc agggtcggaa caggagagcg cacgagggag   3000
cttccagggg gaaacgcctg gtatctttat agtcctgtcg ggtttcgcca cctctgactt   3060
gagcgtcgat ttttgtgatg ctcgtcaggg gggcggagcc tatggaaaaa cgccagcaac   3120
gcggcctttt tacggttcct ggccttttgc tggccttttg ctcacatgtt ctttcctgcg   3180
ttatcccctg attctgtgga taaccgtatt accgcctttg agtgagctga taccgctcgc   3240
cgcagccgaa cgaccgagcg cagcgagtca gtgagcgagg aagcggaaga gcgcctgatg   3300
cggtattttc tccttacgca tctgtgcggt atttcacacc gcatatggtg cactctcagt   3360
acaatctgct ctgatgccgc atagttaagc cagtatacac tccgctatcg ctacgtgact   3420
gggtcatggc tgcgccccga cacccgccaa cacccgctga cgcgccctga cgggcttgtc   3480
tgctcccggc atccgcttac agacaagctg tgaccgtctc cgggagctgc atgtgtcaga   3540
ggttttcacc gtcatcaccg aaacgcgcga ggcagcagat caattcgcgc gcgaaggcga   3600
```

-continued

```
agcggcatgc ataatgtgcc tgtcaaatgg acgaagcagg gattctgcaa accctatgct   3660

actccgtcaa gccgtcaatt gtctgattcg ttaccaatta tgacaacttg acggctacat   3720

cattcacttt ttcttcacaa ccggcacgga actcgctcgg gctggccccg gtgcattttt   3780

taaatacccg cgagaaatag agttgatcgt caaaaccaac attgcgaccg acggtggcga   3840

taggcatccg ggtggtgctc aaaagcagct tcgcctggct gatacgttgg tcctcgcgcc   3900

agcttaagac gctaatccct aactgctggc ggaaaagatg tgacagacgc gacggcgaca   3960

agcaaacatg ctgtgcgacg ctggcgatat caaaattgct gtctgccagg tgatcgctga   4020

tgtactgaca agcctcgcgt acccgattat ccatcggtgg atggagcgac tcgttaatcg   4080

cttccatgcg ccgcagtaac aattgctcaa gcagatttat cgccagcagc tccgaatagc   4140

gcccttcccc ttgcccggcg ttaatgattt gcccaaacag gtcgctgaaa tgcggctggt   4200

gcgcttcatc cgggcgaaag aaccccgtat tggcaaatat tgacggccag ttaagccatt   4260

catgccagta ggcgcgcgga cgaaagtaaa cccactggtg ataccattcg cgagcctccg   4320

gatgacgacc gtagtgatga atctctcctg gcgggaacag caaaatatca cccggtcggc   4380

aaacaaattc tcgtccctga tttttcacca ccccctgacc gcgaatggtg agattgagaa   4440

tataaccttt cattcccagc ggtcggtcga taaaaaaatc gagataaccg ttggcctcaa   4500

tcggcgttaa acccgccacc agatgggcat taaacgagta tcccggcagc aggggatcat   4560

tttgcgcttc agccatactt ttcatactcc cgccattcag ag                      4602
```